(12) United States Patent
Qi et al.

(10) Patent No.: US 6,743,888 B1
(45) Date of Patent: Jun. 1, 2004

(54) POLYCARBONATES

(75) Inventors: Yu Qi, Oakville (CA); Nan-Xing Hu, Oakville (CA); H. Bruce Goodbrand, Hamilton (CA)

(73) Assignee: Xerox Corporation, Stamford, CT (US)

( * ) Notice: Subject to any disclaimer, the term of this patent is extended or adjusted under 35 U.S.C. 154(b) by 93 days.

(21) Appl. No.: 10/390,061

(22) Filed: Mar. 14, 2003

(51) Int. Cl.[7] ............................................. C08G 64/00
(52) U.S. Cl. ....................................... 528/198; 528/196
(58) Field of Search ................................. 528/196, 198

(56) References Cited

U.S. PATENT DOCUMENTS

| | | | |
|---|---|---|---|
| 4,265,990 A | 5/1981 | Stolka et al. | 430/59 |
| 4,587,189 A | 5/1986 | Hor et al. | 430/59 |
| 5,482,811 A | 1/1996 | Keoshkerian et al. | 430/135 |
| 5,493,016 A | 2/1996 | Burt et al. | 540/139 |
| 5,645,965 A | 7/1997 | Duff et al. | 430/59 |
| 5,871,877 A | 2/1999 | Ong et al. | 430/59 |
| 5,874,193 A | 2/1999 | Liu et al. | 430/59 |
| 6,214,505 B1 | 4/2001 | Ong et al. | 430/58.65 |
| 6,287,737 B1 | 9/2001 | Ong et al. | 430/58.8 |

*Primary Examiner*—Terressa Boykin
(74) *Attorney, Agent, or Firm*—E. D. Palallo

(57) ABSTRACT

A polycarbonate containing a repeating segment represented by Formula (I)

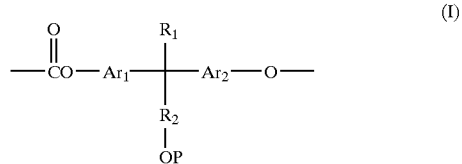

wherein $R_1$ is selected from the group consisting of hydrogen, alkyl, aryl; $R_2$ represents a divalent linkage selected from the group consisting of alkylene containing one or more heteroatoms of halogen, nitrogen, oxygen, sulfur, silicon, and phosphorus, arylalkylene, and arylene; $Ar_1$ and $Ar_2$ each independently represent aromatic groups; and P represents a hydrogen atom, or a hydroxyl protective group.

39 Claims, No Drawings

POLYCARBONATES

COPENDING APPLICATIONS AND PATENTS

Illustrated in U.S. Ser. No. 10,390,057, filed concurrently herewith on Photoconductive Imaging Members, the disclosure of which is totally incorporated herein by reference is a photoconductive imaging member comprised of a photogenerating layer, and a charge transport layer, and wherein the charge transport layer comprises a polycarbonate component containing a repeating segment of the formula

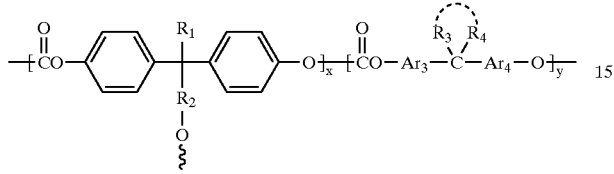

wherein $R_1$ is selected from the group consisting of hydrogen, alkyl and aryl; $R_2$ represents a divalent linkage; $Ar_3$ and $Ar_4$ each independently represent aromatic groups; $R_3$ and $R_4$ are independently selected from the group consisting of hydrogen, alkyl, and aryl; and wherein x and y represent the mole fractions of the repeating segments; and in U.S. Ser. No. 10/389,858, filed concurrently herewith on Photoconductive Imaging Members, the disclosure of which is totally incorporated herein by reference is a photoconductive imaging member comprised of a photogenerating layer, and a charge transport layer, and wherein the charge transport layer comprises a crosslinked polycarbonate component comprised of

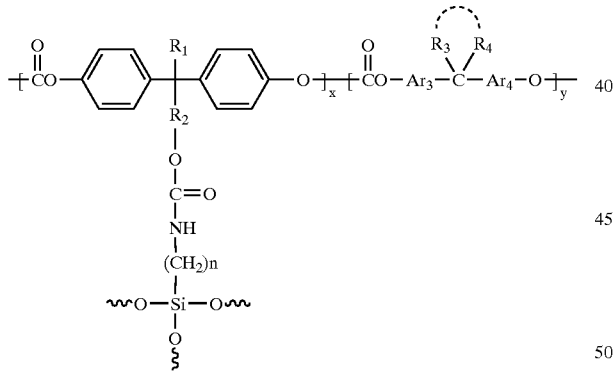

wherein $R_1$ is selected from the group consisting of hydrogen, alkyl, a halogenated alkyl, and aryl; $R_2$ represents a divalent linkage; $Ar_3$ and $Ar_4$ each independently represent aromatic groups; $R_3$ and $R_4$ are independently selected from the group consisting of hydrogen, alkyl and aryl; n represents the number of segments; and wherein x and y are the mole fractions of the repeating segments with the value of x+y being equal to 1.

Illustrated in U.S. Pat. No. 6,214,505, the disclosure of which is totally incorporated herein by reference, is a photoconductive imaging member comprised of a photogenerating layer and a charge transport layer, and wherein the charge transport layer contains a poly(imide-carbonate) resin binder of (I) or (II)

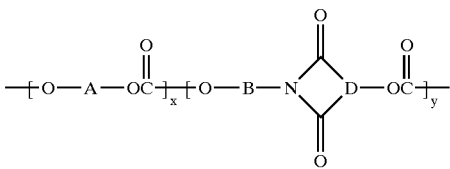

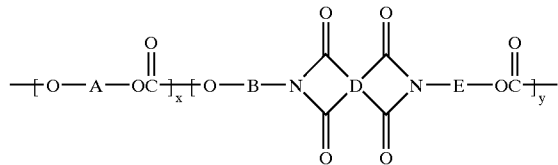

wherein A, B and E are divalent linkages; D is a trivalent linkage in (I) and a tetravalent linkage in (II); and x and y represent mole fractions wherein the sum of x+y is equal to 1.

Illustrated in U.S. Pat. No. 5,645,965, the disclosure of which is totally incorporated herein by reference, are photoconductive imaging members with perylenes and a number of charge transports, such as amines.

Illustrated in U.S. Pat. No. 6,287,737, the disclosure of which is totally incorporated herein by reference, is a photoconductive imaging member comprised of a supporting substrate, a hole blocking layer thereover, a photogenerating layer and a charge transport layer, and wherein the hole blocking layer is comprised of a crosslinked polymer derived from the reaction of a silyl-functionalized hydroxyalkyl, polymer of Formula (I) with an organosilane of Formula (II) and water

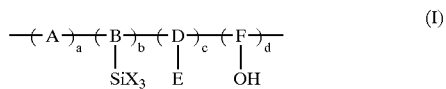

wherein A, B, D, and F represent the segments of the polymer backbone; E is an electron transporting moiety; X is selected from the group consisting of chloride, bromide, iodide, cyano, alkoxy, acyloxy, and aryloxy; a, b, c, and d are mole fractions of the repeating monomer units such that the sum of a+b+c+d is equal to 1; R is alkyl, substituted alkyl, aryl, or substituted aryl, with the substituent being halide, alkoxy, aryloxy, and amino; and $R^1$, $R^2$, and $R^3$ are independently selected from the group consisting of alkyl, aryl, alkoxy, aryloxy, acyloxy, halogen, cyano, and amino, subject to the provision that two of $R^1$, $R^2$, and $R^3$ are independently selected from the group consisting of alkoxy, aryloxy, acyloxy, and halide.

Illustrated in U.S. Pat. No. 5,874,193, the disclosure of which is totally incorporated herein by reference, are photoconductive imaging members with a hole blocking layer comprised of a crosslinked polymer derived from crosslinking a alkoxysilyl-functionalized polymer bearing an electron transporting moiety. In U.S. Pat. No. 5,871,877, the disclosure of which is totally incorporated herein by reference, there are illustrated multilayered imaging members with a solvent resistant hole blocking layer comprised of a crosslinked electron transport polymer derived from crosslinking a thermally crosslinkable alkoxysilyl, acyloxysilyl or halosilyl-functionalized electron transport polymer with an alkoxysilyl, acyloxysilyl or halosilyl compound, such as alkyltrialkoxysilane, alkyltrihalosilane, alkylacyloxysilane, aminoalkyltrialkoxysilane, and the like, in contact with a supporting substrate and situated between the supporting substrate and the photogenerating layer comprised of the photogenerating pigments of U.S. Pat. No. 5,482,811, the disclosure of which is totally incorporated herein by reference, especially Type V hydroxygallium phthalocyanine.

Illustrated in U.S. Pat. No. 5,493,016, the disclosure of which is totally incorporated herein by reference, are imaging members comprised of a supporting substrate, a photogenerating layer of hydroxygallium phthalocyanine, a charge transport layer, a perylene photogenerating layer, which is preferably a mixture of bisbenzimidazo(2,1-a-1', 2'-b)anthra(2,1,9-def:6,5,10-d'e'f')diisoquinoline-6,11-dione and bisbenzimidazo(2,1-a:2',1'-a)anthra(2,1,9-def:6,5,10-d'e'f')diisoquinoline-10,21-dione, reference U.S. Pat. No. 4,587,189, the disclosure of which is totally incorporated herein by reference; and as a top layer a second charge transport layer.

Further, illustrated in U.S. Pat. No. 5,645,965, the disclosure of which is totally incorporated herein by reference, are symmetrical perylene photoconductive members.

A number of the appropriate components and processes of the above recited patent applications and patents may be selected for the present invention in embodiments thereof.

BACKGROUND

This invention is generally directed to imaging members containing polycarbonates, and more specifically, the present invention is directed to multilayered photoconductive imaging members containing charge, especially hole transport binders comprised of crosslinked polycarbonates, which can be formed from the reaction of novel polycarbonates containing pendant hydroxyl groups along the polymer backbone, and functional agents comprised of, for example, isocyanates.

A number of advantages are associated with the present invention in embodiments thereof, such as excellent electrical characteristics, the provision of robust photoconductive imaging members wherein the life thereof is increased from about 170 kilocycles to over 500 kilocycles, and more specifically, from about 255 to about 510 kilocycles; compatibility with hole transport components, such as aryl amines; resistance to solvents, such as methylene chloride, tetrahydrofuran, and chlorobenzene, and substantial resistant to the disintegration of bias charging rolls. In embodiments of the present invention, the imaging members exhibit excellent cyclic/environmental stability, and substantially no adverse changes in their performance over extended time periods, and excellent resistance to mechanical abrasion, and therefore extended photoreceptor life. The aforementioned photoresponsive, or photoconductive imaging members can be positively or negatively charged when the photogenerating layer is situated between the charge transport layer and the substrate.

Processes of imaging, especially xerographic imaging and printing, including digital, are also encompassed by the present invention. More specifically, the layered photoconductive imaging members of the present invention can be selected for a number of different known imaging and printing processes including, for example, color processes, digital imaging process, digital printers, PC printers, and electrophotographic imaging processes, especially xerographic imaging and printing processes wherein charged latent images are rendered visible with toner compositions of an appropriate charge polarity. The imaging members of the present invention are in embodiments sensitive in the wavelength region of, for example, from about 500 to about 900 nanometers, and more specifically, from about 650 to about 850 nanometers, thus diode lasers can be selected as the light source. Moreover, the Imaging members of this invention are useful for color xerographic systems.

REFERENCES

Layered photoresponsive imaging members have been described in numerous U.S. patents, such as U.S. Pat. No. 4,265,990, the disclosure of which is totally incorporated herein by reference, wherein there is illustrated an imaging member comprised of a photogenerating layer, and an aryl amine hole transport layer. Examples of photogenerating layer components include trigonal selenium, metal phthalocyanines, vanadyl phthalocyanines, and metal free phthalocyanines. Additionally, there is described in U.S. Pat. No. 3,121,006, the disclosure of which is totally incorporated herein by reference, a composite xerographic photoconductive member comprised of finely divided particles of a photoconductive inorganic compound dispersed in an electrically insulating organic resin binder. The binder materials disclosed in the '006 patent comprise a material which is incapable of transporting for any significant distance injected charge carriers generated by the photoconductive particles.

The use of perylene pigments as photoconductive substances is also known. There is thus described in Hoechst European Patent Publication 0040402, DE3019326, filed May 21, 1980, the use of N,N'-disubstituted perylene-3,4,9,10-tetracarboxyldiimide pigments as photoconductive substances. Specifically, there is, for example, disclosed in this publication N,N'-bis(3-methoxypropyl)perylene-3,4,9,10-tetracarboxyl-diimide dual layered negatively charged photoreceptors with improved spectral response in the wavelength region of 400 to 700 nanometers. A similar disclosure is presented in Ernst Gunther Schlosser, *Journal of Applied Photographic Engineering*, Vol. 4, No. 3, page 118 (1978). There are also disclosed in U.S. Pat. No. 3,871,882 photoconductive substances comprised of specific perylene-3,4,9,10-tetracarboxylic acid derivative dyestuffs. In accordance with this patent, the photoconductive layer is preferably formed by vapor depositing the dyestuff in a vacuum. Also, there are specifically disclosed in this patent dual layer photoreceptors with perylene-3,4,9,10-tetracarboxylic acid diimide derivatives, which have spectral response in the wavelength region of from 400 to 600 nanometers. Also, in U.S. Pat. No. 4,555,463, the disclosure of which is totally incorporated herein by reference, there is illustrated a layered imaging member with a chloroindium phthalocyanine photogenerating layer. In U.S. Pat. No. 4,587,189, the disclosure of which is totally incorporated herein by reference, there is illustrated a layered imaging member with, for example, a perylene, pigment photogenerating component. Both of the aforementioned patents disclose an aryl amine component, such as N,N'-diphenyl-N,N'-bis(3-methylphenyl)-1,1'-biphenyl-4,4'-diamine dispersed in a polycarbonate binder, as a hole transport layer. The above components, such as the photogeneraling compounds and the aryl amine charge transport, can be selected for the imaging members of the present invention.

SUMMARY

It is a feature of the present invention to provide novel polycarbonates and imaging members thereof with many of the advantages illustrated herein, such as for example extended life, and excellent Imaging performance.

A further feature of the present invention is the provision of novel polycarbonates, and improved layered photoresponsive imaging members which are responsive to near infrared radiation exposure and which imaging members in embodiments possess excellent wear resistance.

In a further feature of the present invention there are provided imaging members containing crosslinked binder layers which are compatible with transport layer components, and more specifically, wherein the polycarbonate binder, inclusive of the crosslinked components thereof, are miscible with hole transport molecules, such as arylamines, and wherein the photoconductive imaging member possesses excellent electrical performance including high charge acceptance, low dark decay and low residual charge.

Moreover, in another feature of the present invention there are provided abrasion resistant photoconductive imaging members, and wherein the imaging member corrosive erosion by bias charging rolls and mechanical erosion by cleaning blades is avoided or minimized.

Aspects of the present invention relate to novel polycarbonates; a polycarbonate comprised of a repeating segment represented by Formula (I)

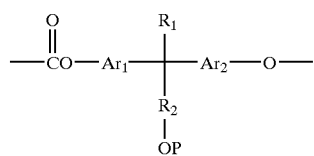

wherein $R_1$ is selected from the group consisting of hydrogen, alkyl, and aryl; $R_2$ represents a divalent linkage selected from the group consisting of alkylene optionally containing one or more heteroatoms of halogen, nitrogen, oxygen, sulfur, silicon, or phosphorus, arylalkylene, and arylene; $Ar_1$ and $Ar_2$ each independently represent aromatic groups; and P represents a hydrogen atom, or a hydroxyl protective group; a polycarbonate wherein arylene is selected from the group consisting of

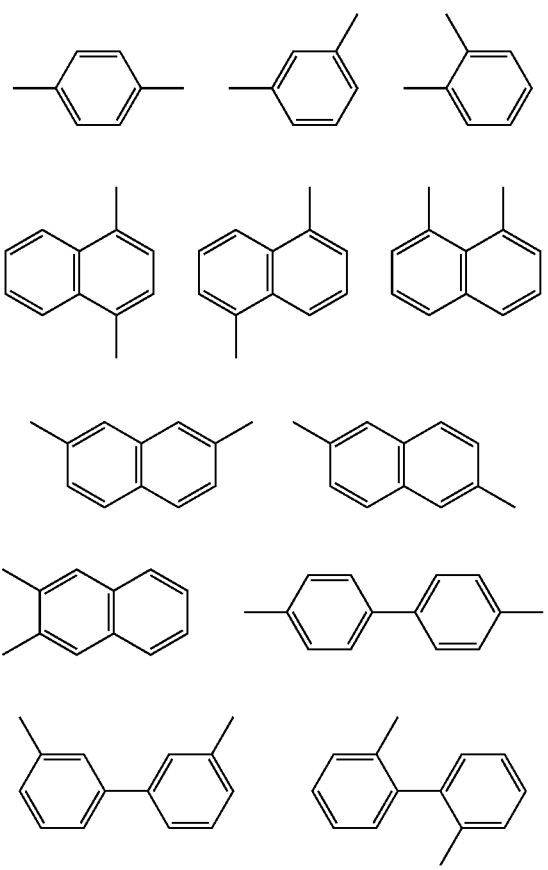

and wherein the arylene optionally contains a substituent selected from the group consisting of hydrogen, halogen, alkyl of from 1 to about 15 carbon atoms, halogenated alkyl of 1 to about 15 carbons, or alkyl containing one or more heteroatoms of nitrogen, oxygen, sulfur, silicon, or phosphorus; a polycarbonate containing at least one repeating segment represented by Formula (II)

wherein A is a divalent hydrocarbon optionally containing from about 2 to about 30 carbon atoms, or optionally a divalent hydrocarbon linkage containing from about 2 to about 30 carbon atoms further containing a heteroatom of oxygen, nitrogen, sulfur, silicon, or phosphorus and wherein $R_1$ is selected from the group consisting of hydrogen, alkyl, and aryl; a polycarbonate wherein A is selected from the group comprised of

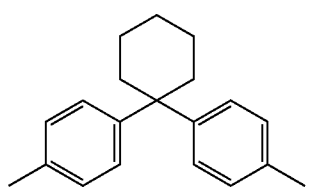

-continued

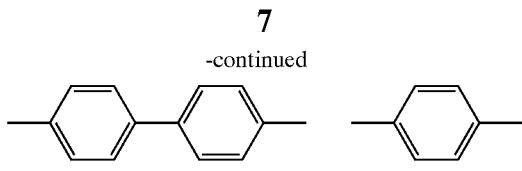
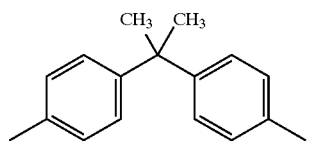
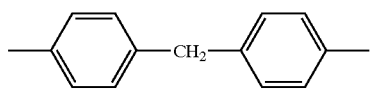

-continued

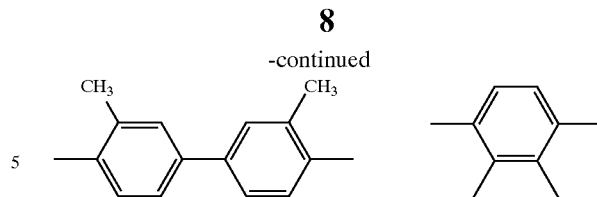
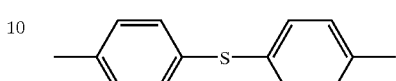
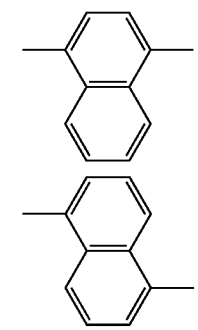

—CH₂CH₂—  —CH₂CH₂CH₂CH₂—  —CH₂CH₂OCH₂CH₂—;

a polycarbonate and wherein the polycarbonate is comprised of

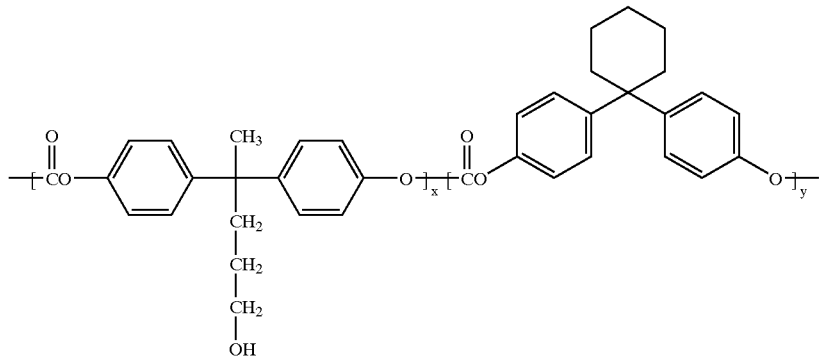

(III-a)

-continued

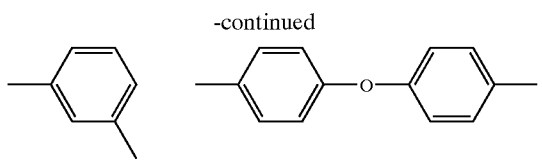
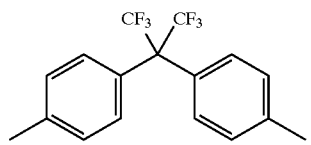
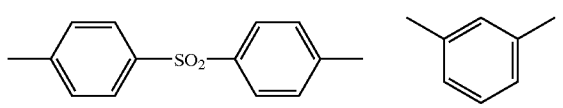
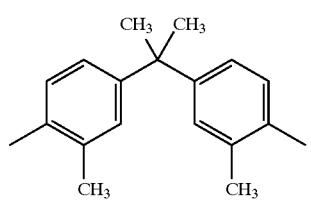

wherein x and y represent mole fractions such that x+y is equal to 1, and wherein the polycarbonate possesses a weight $M_w$ average molecular weight of from about 2,000 to about 500,000; a monomer comprised of

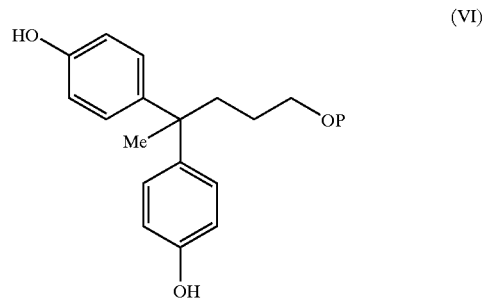

(VI)

wherein P is a protective group selected from the group consisting of a pyranyl, a thiopyranyl, an alkoxyalkyl, an alkylsilyl, an alkylarylsilyl, an acyl, and a benzyl; a polycarbonate of the formula

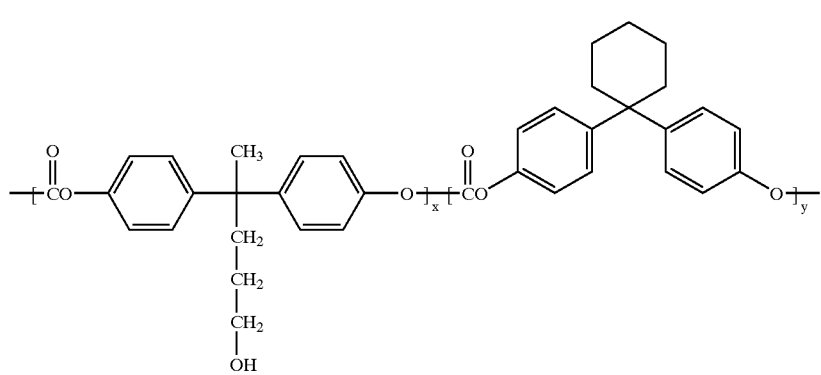
(III-a)
wherein x is about 0.05 and y is about 0.95; wherein x is about 0.10 and y is about 0.90; wherein x is about 0.15 and y is about 0.85; wherein x is about 0.20 and y is about 0.80; or wherein x is about 0.30 and y is about 0.70; a monomer and the alternative formulas
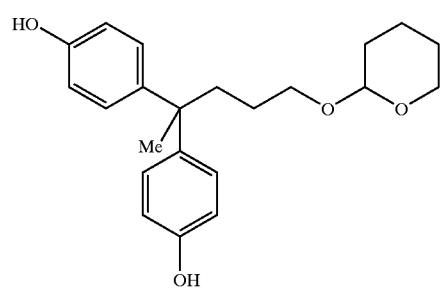
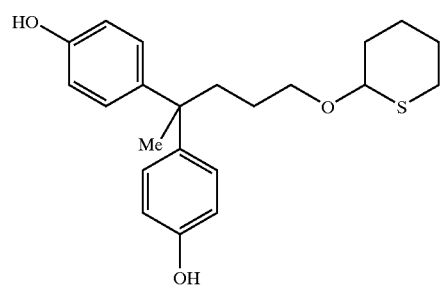
-continued
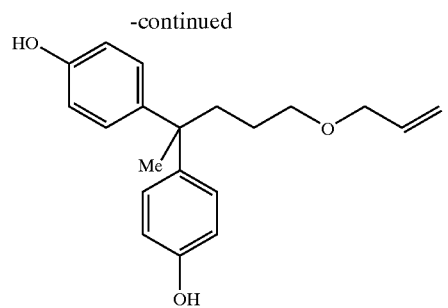
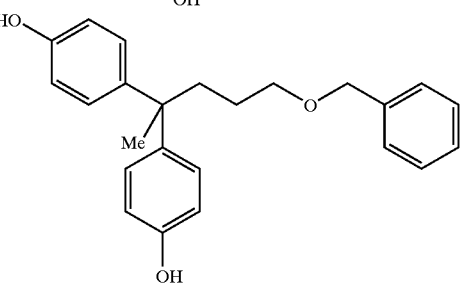
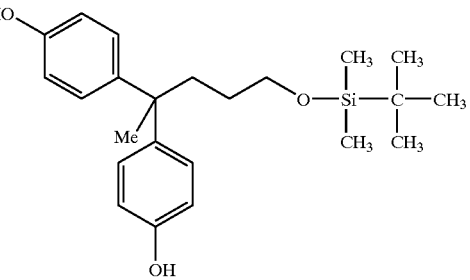
a crosslinked polycarbonate wherein the polymer is alternatively
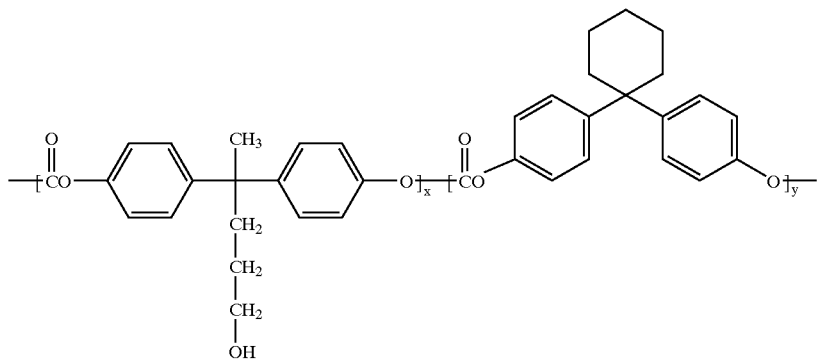

-continued

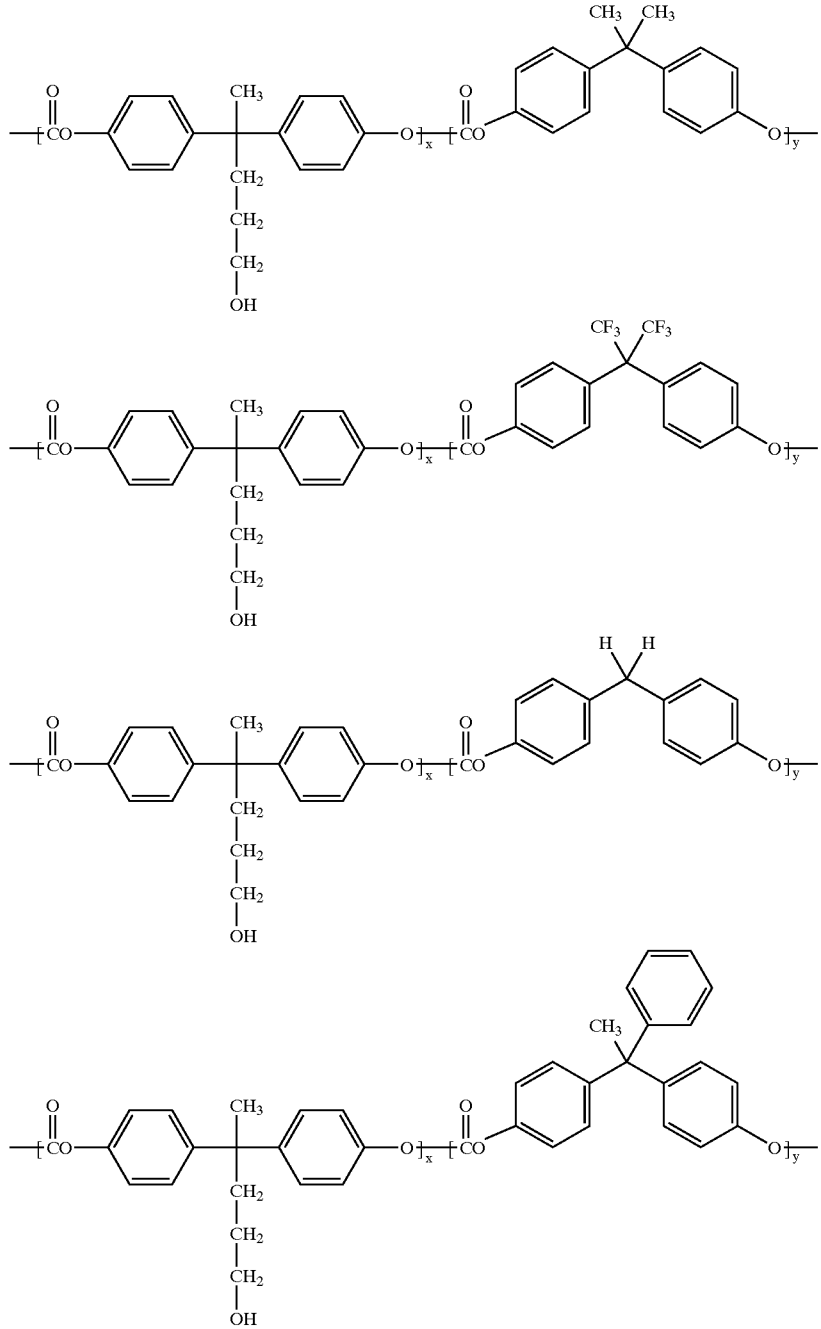

a photoconductive imaging member comprised of a supporting substrate, a blocking layer, a photogenerating layer, and a charge transport layer, and wherein the charge transport layer comprises a hole transport component and a crosslinked polycarbonate binder; a photoconductive imaging member comprised in sequence of a supporting substrate, a photogenerating layer, a charge transport layer containing hole transport aryl amine molecules and a crosslinked polycarbonate binder, wherein the crosslinked polycarbonate is formed by reacting a hydroxyl-pendent polycarbonate with an isocyanate; a photoconductive imaging member comprised of a supporting substrate, a hole blocking layer thereover, a photogenerating layer, and a charge transport layer containing a polycarbonate with hydroxyl groups and/or crosslinked components thereof; a photoconductive imaging member wherein the photogenerating layer is comprised of photogenerating pigments dispersed in a resinous binder, which pigments are present in an amount of from about 5 percent by weight to about 95 percent by weight; a photoconductive imaging member wherein the photogenerating resinous binder is selected from the group consisting of polyesters, polyvinyl butyrals, polycarbonates, polystyrene-b-polyvinyl pyridine, and polyvinyl formals; a photoconductive imaging member wherein the charge transport layer comprises, aryl amine molecules; a photoconductive imaging member wherein the aryl amines are of the formula

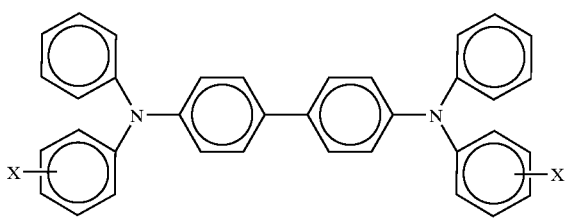

wherein X is selected from the group consisting of alkyl and halogen; a photoconductive imaging member wherein the arylamine alkyl contains from about 1 to about 10 carbon atoms; a photoconductive imaging member wherein the arylamine alkyl contains from 1 to about 5 carbon atoms; a photoconductive imaging member wherein the arylamine alkyl is methyl, and wherein halogen is chlorine; a photoconductive imaging member wherein the aryl amine is N,N'-diphenyl-N,N-bis(3-methylphenyl)-1,1'-biphenyl-4,4'-diamine; a photoconductive imaging member further including an adhesive layer of a polyester with an $M_w$ of preferably about 70,000, and an $M_n$ of from about 25,000 to about 50,000, and preferably about 35,000; a photoconductive imaging member wherein the photogenerating layer is comprised of metal phthalocyanines, or metal free phthalocyanines; a photoconductive imaging member wherein the photogenerating layer is comprised of titanyl phthalocyanines, perylenes, or hydroxygallium phthalocyanines; a photoconductive imaging member wherein the photogenerating layer is comprised of Type V hydroxygallium phthalocyanine; a method of imaging which comprises generating an electrostatic latent image on the imaging member, developing the latent image, and transferring the developed electrostatic image to a suitable substrate; imaging members comprised of a supporting substrate thereover, a photogenerating layer of, for example, hydroxygallium phthalocyanine, and a charge transport layer containing the polycarbonates illustrated herein; a photoconductive imaging member comprised of a blocking layer, a photogenerating layer, and a charge transport layer, and wherein the charge transport layer comprises hole transport components and a crosslinked polycarbonate binder of the formula (I)

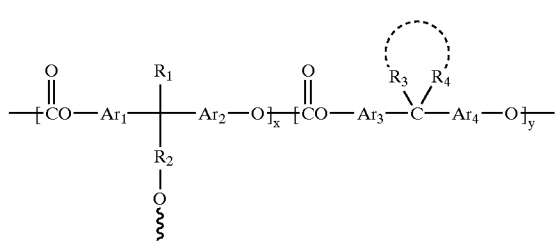

wherein, for example, $R_1$ is selected from the group consisting of hydrogen, alkyl of, for example, from about 1 to about 15 carbons, a halogenated alkyl of from about 1 to about 15 carbons, an alkyl with, for example, from about 1 to about 15 carbons optionally further containing one or more heteroatoms selected, for example, from the group consisting of nitrogen, oxygen, sulfur, silicon, and phosphorus, an aryl or substituted aryl of, for example, from about 6 to about 30 carbons; $R_2$ represents a divalent link of, for example, an alkylene with from about 1 to about 15 carbons; $Ar_1$, $Ar_2$, $Ar_3$ and $Ar_4$ each independently represent aromatic groups of from about 6 to about 30 carbons; $R_3$ and $R_4$ are independently selected from the group consisting of hydrogen, alkyl of from about 1 to about 15 carbons, aryl or substituted aryl of from about 6 to about 30 carbons, wherein $R_3$ and $R_4$ may form a combined ring structure containing from about 5 to about 20 atoms; and wherein x and y represent the mole fractions of the repeating segments with the sum of x and y being equal to about 1, and more specifically, wherein x and y can each be from about 0.03 to about 1; crosslinked polycarbonates generated from a hydroxy-pendent polycarbonate represented by the general Formula (II)

(II)

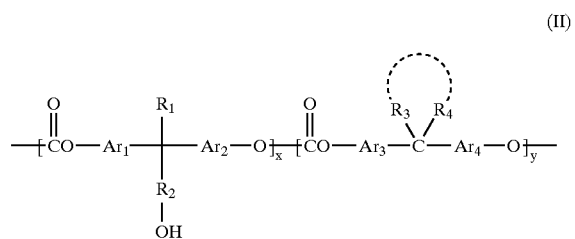

wherein $R_1$ is selected from the group consisting of hydrogen throughout (for example, is intended for all examples of substituents and for the number of carbon atoms), alkyl of from about 1 to about 15 carbons, a halogenated alkyl of from about 1 to about 15 carbons, an alkyl of from about 1 to about 15 carbons further containing one or more heteroatoms selected from the group consisting of nitrogen, oxygen, sulfur, silicon, and phosphorus, an aryl or substituted aryl of from about 6 to about 30 carbons; $R_2$ represents a divalent linkage; H can be P which represents a hydrogen atom, or a hydroxyl protective group; $Ar_1$, $Ar_2$, $Ar_3$ and $Ar_4$ each independently represent aromatic groups of from about 6 to about 30 carbons; $R_3$ and $R_4$ are independently selected from the group consisting of hydrogen, alkyl of from about 1 to about 15 carbons, aryl or substituted aryl of from about 6 to about 30 carbons, wherein $R_3$ and $R_4$ may form a combined ring structure containing from about 5 to about 20 atoms, wherein x and y represent the mole fractions of the repeating segment; and wherein, for example, the weight average molecular weight, $M_w$, and the number average molecular weight, $M_n$, thereof are, for example, from about 1,000 to about 1,000,000, and more specifically, $M_w$ is preferably from about 1,000 to about 200,000 and $M_n$ is preferably from about 500 to about 100,000; and a monomer comprised of (VI)

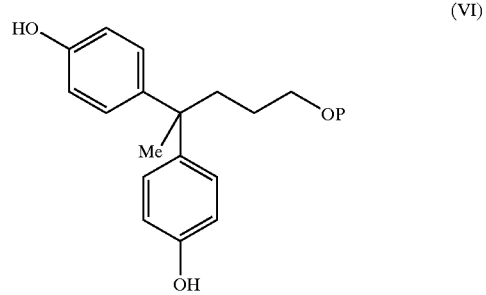

wherein P is a protective group selected from the group consisting of a pyranyl, a thiopyranyl, an alkoxyalkyl, an alkylsilyl, an alkylarylsilyl, an acyl, and a benzyl.

Examples of $R_1$ include suitable substituents such as a hydrogen atom; alkyl with 1 to about 30 carbon atoms, such as methyl, ethyl, propyl, butyl, iso-propyl, tert-butyl and the like; aryl with 6 to about 30 carbon atoms, such as phenyl, naphthyl, phenaphthyl, biphenyl, and the like. The alkyl group may contain halogen atoms such as fluoride, chloride, or bromide. Illustrative examples of halogenated alkyl are fluoromethyl, fluoroethyl, perfluoropropyl, fluorobutyl, fluoropentyl, chloromethyl, chloroethyl, and the like.

Examples of divalent linkages include suitable substituents such as alkylene, arylene, alkylenearyl groups, and more specifically, alkylene with 1 to about 30 carbon atoms, and more specifically, about 1 to about 10, such as methylene, ethylene, trimethylene, tetramethylene, pentamethylene, hexamethylene, and the like; arylene with 6 to about 30 carbon atoms, such as phenylene, biphenylene, naphthalene, and the like; and alkylenearyl containing from about 13 to about 60 carbon atoms, such as methylenephenyl, methylenediphenyl, ethylenephenyl, propylenephenyl, and the like.

Examples of $R_3$ and $R_4$ include suitable substituents such as a hydrogen atom; alkyl having 1 to about 30 carbon atoms, such as methyl, ethyl, propyl, butyl, iso-propyl, tert-butyl and the like; substituted alkyl including halogen, such as fluoride, chloride, and bromide, and alkoxy, such as methoxy, ethoxy, propoxy, iso-propoxy, butoxy and the like. Typical examples of substituted alkyl include fluoromethyl, fluoroethyl, fluoropropyl, chlorobutyl, methoxymethyl, ethoxymethyl and the like. Examples of aryl include those with 6 to about 30 carbon atoms, such as phenyl, biphenyl, naphthyl, and the like; and substituted aryl with 6 to about 30 carbon atoms. Illustrative examples of substituted aryl are methylphenyl, ethylphenyl, propylphenyl, butylphenyl, dimethylphenyl, trimethylphenyl, tetramethylphenyl and the like. The substituted aryl may additionally contain halogen atoms such as fluoride, chloride, or bromide. Illustrative examples include trifluoromethylphenyl, chlorophenyl, perfluorophenyl, fluorophenyl, dichlorophenyl, and the like. Illustrative examples of the ring structures $R_3$ and $R_7$ include cyclopropyl, cyclobutyl, cyclohexyl, cyclopentyl, cyclooctyl, and the like.

Examples of $Ar_1$, $Ar_2$, $Ar_3$, and $Ar_4$ and the substituted derivatives thereof with alkyl or halogen include aryl with 6 to about 60 carbon atoms, such as phenyl, biphenyl, naphthyl, methylenephenyl, dimethylenephenyl, binaphthyl and the like. Aryl may contain an alkyl substituent such as methyl, ethyl, isopropyl and the like; a halogen substituent such as fluorine, chlorine, or bromine. Illustrative examples of halogenated aryl are fluorophenyl, perfluorophenyl, fluoromethylphenyl, fluoropropylphenyl, chlorophenyl, dichlorophenyl, and the like.

Illustrative examples of hydroxyl-pendent polycarbonates are represented by (IIa) through (IIj) wherein x and y are the molar fractions of the repeating monomer units such that the sum of x+y is, for example, equal to 1, and more specifically, wherein x represents the number of repeating segments, such as a number of from about 0.01 to about 1, and yet more specifically, from about 0.03 to about 0.99.

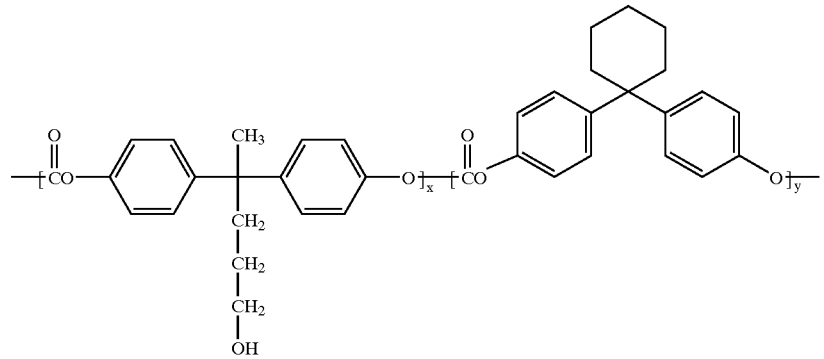

(IIa)

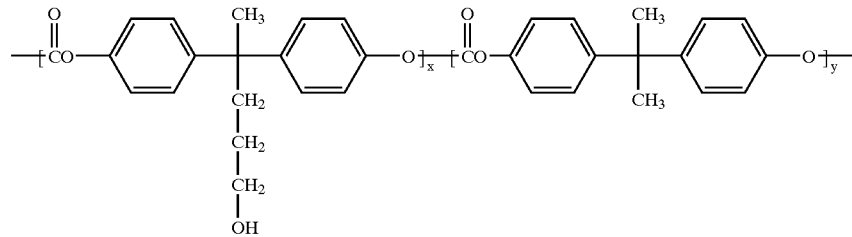

(IIb)

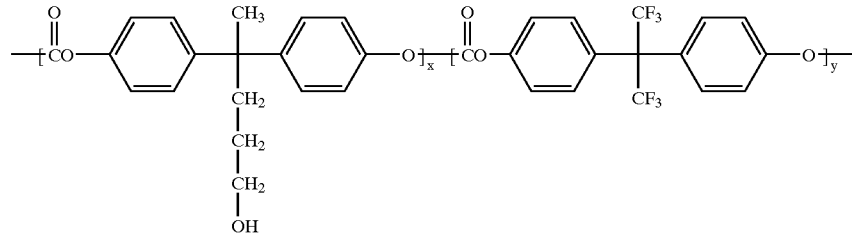

(IIc)

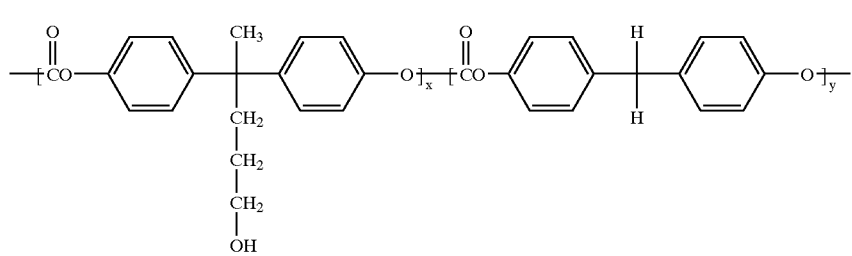
(IId)
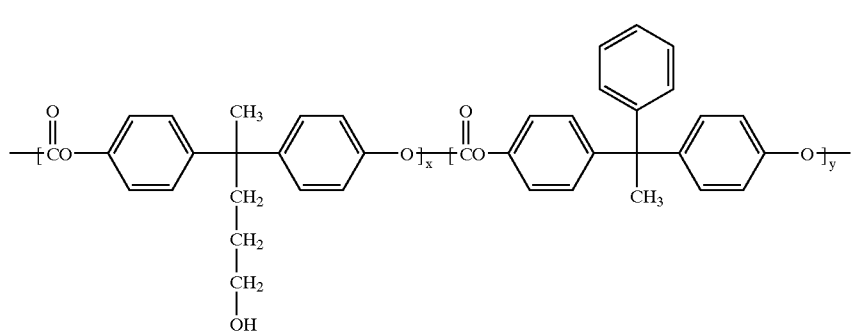
(IIe)
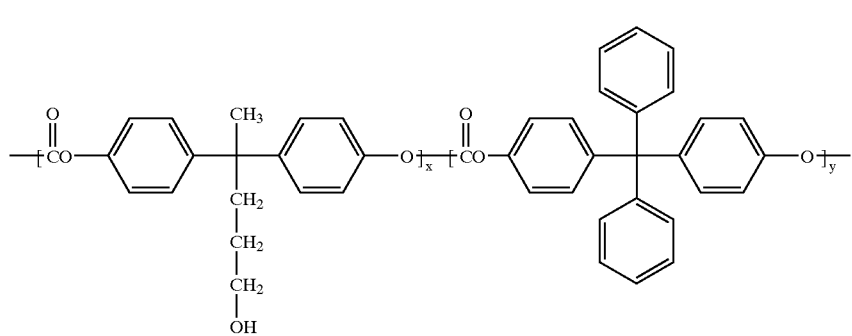
(IIf)
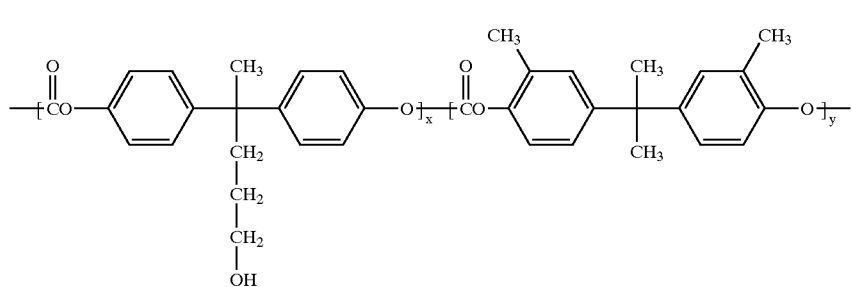
(IIg)
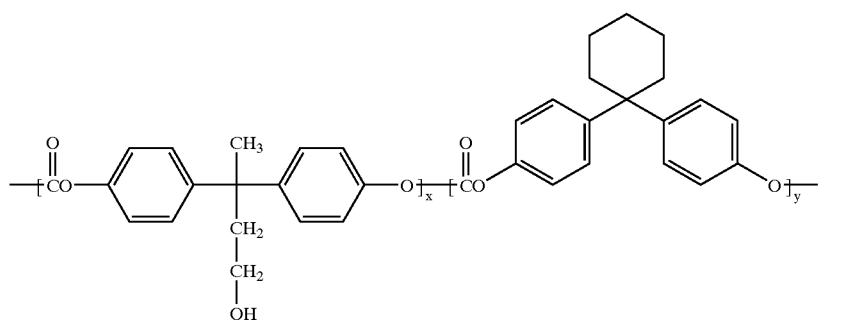
(IIh)

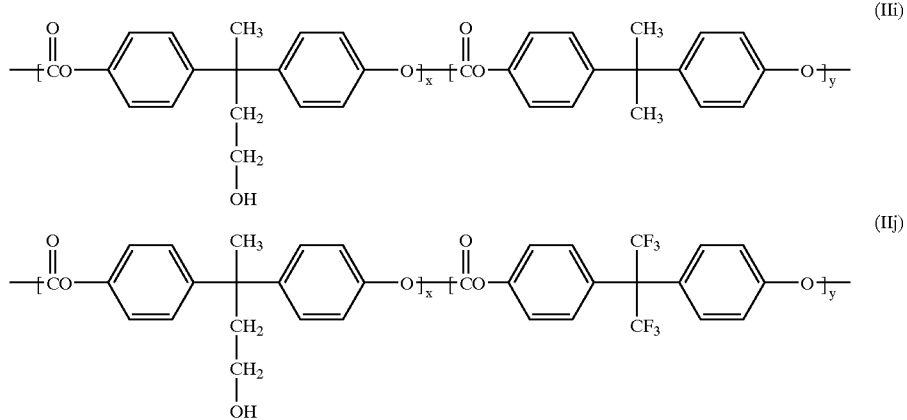

In embodiments, the present invention relates to the provision of a polycarbonate, especially crosslinked polycarbonate, binder illustrated herein. More specifically, the crosslinked polycarbonate (III) can be formed from the reaction of a hydroxyl-pendent polycarbonate of Formula (II) with a curing agent of, for example, a diisocyanate, ONC-L-NCO, and which reaction is illustrated in Scheme (I)

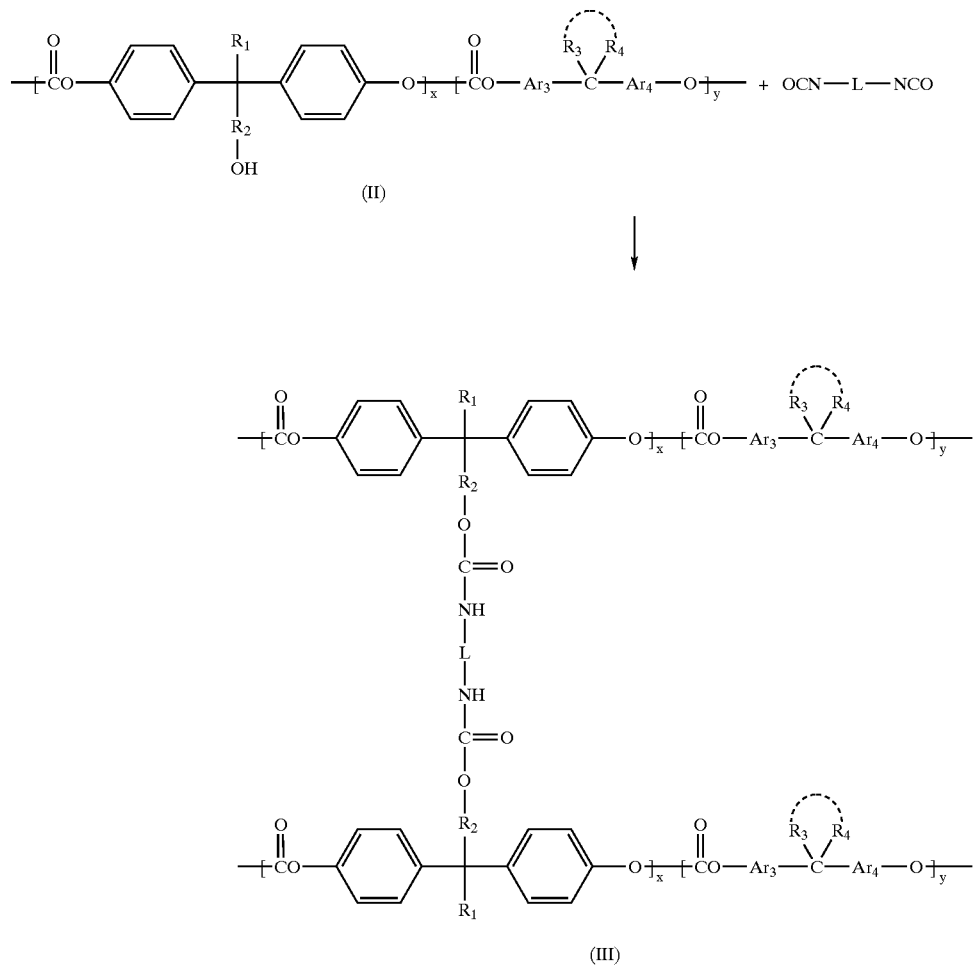

wherein $R_1$, $R_2$, $R_3$, $R_4$, $Ar_3$ and $Ar_4$ are as illustrated herein; and wherein L represents a divalent linkage of, for example, from about 1 to about 30 carbon atoms, and preferably from about 3 to about 15 carbon atoms. Diisocyanate examples include 1,6-diisocyanatohexane, 1,4-diisocyanatobutane, 1,8-diisocyanatooctane, 1,12-diisocyanatododecane, 1,5-diisocyanoto-2-methylpentane, trimethyl-1,6-diisocyanatohexane, 1,3-bis(isocyanatomethyl)cyclohexane, trans-1,4-cyclohexenediisocyanate, 4,4'-methylenebis(cyclohexylisocyanate), isophoronediisocyanate, 1,3-phenylenediisocyanate, 1,4-phenylenediisocyanate, tolylene 2,4-diisocyanate, tolylene 2,6-diisocyanate, 4,4'-methylenebis(2,6-diethylphenylisocyanate), or 4,4'-oxybis(phenylisocyanate), and the like.

The diisocyanate amount selected is, for example, from about 0.1 to about 5 equivalents of the hydroxyl group contained in the polycarbonate; the curing reaction can be accomplished by heating at, for example, about room temperature (25° C.) to about 200° C., and preferably from about 50° C. to about 140° C. Optionally a catalyst can be added to assist the crosslinking reaction. Catalyst examples include amines, tin compounds, zinc compounds and the like, with specific examples being triethylamine, tributylamine, dibutyltin diacetate, zinc octate, and the like. The hydroxyl polycarbonates, therefore, can be crosslinked by reacting with isocyanates, and which crosslinked polycarbonate products provide chemical and mechanical wear resistance without altering substantially the electrical performance, and therefore, are used to extend the life of photoresponsive imagining members.

The hydroxyl-pendent polycarbonates (II) can be prepared by known interfacial phosgenation, interfacial or solution polycondensation. More specifically, the polycarbonates can be prepared by the interfacial polycondensation method according to Scheme (II) wherein the substituents, such as R, x and y, are as illustrated herein.

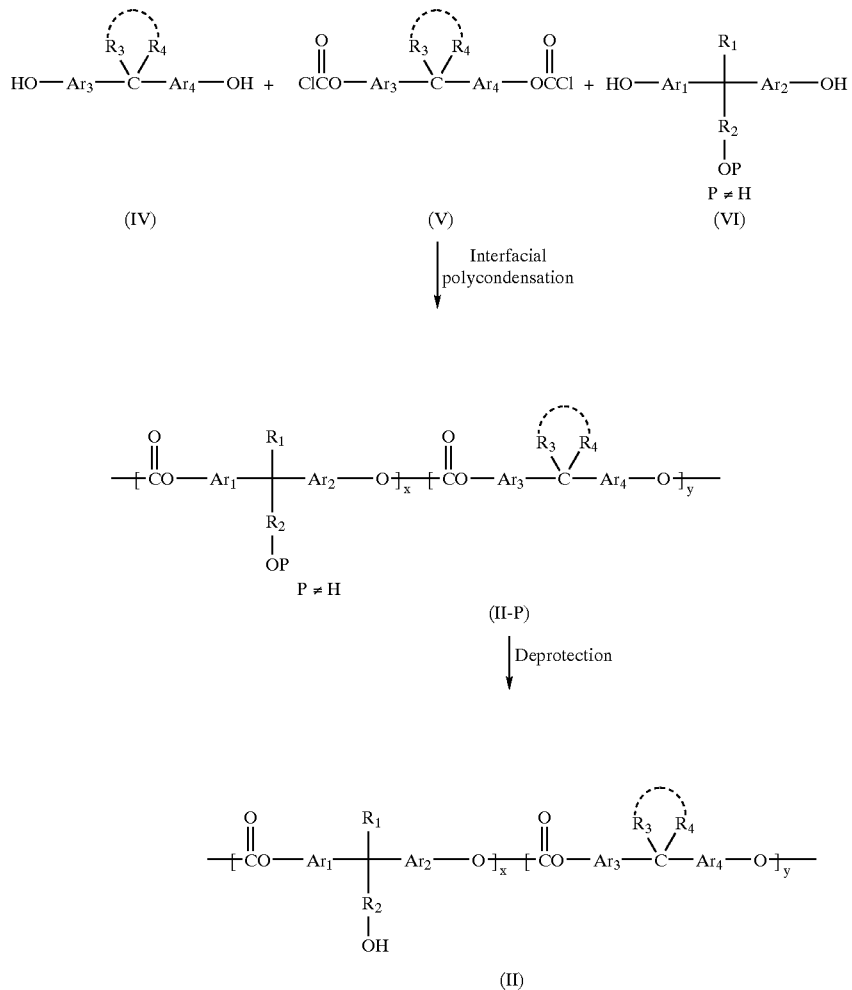

Typically, the processes for the preparation of the polycarbonates are initiated with the preparation of tetrahydropyranyl ether (THP) protected hydroxyl bisphenol monomer (VI), followed by interfacial polycondensation of the protected hydroxyl bisphenol and bischloroformate (V) optionally with other suitable bisphenols (IV) to produce the THP protected hydroxyl polycarbonate (II-P), and then followed by removing the THP protecting group to provide the hydroxyl polycarbonate (III). The hydroxyl group is protected by a THP group which could prevent it from reacting with the bischloroformate to interrupt the polymer formation. Specifically, the monomer can be prepared by the following method as shown in Scheme (III): 4,4-bis(4-hydroxyphenyl)valeric acid (VII) is refluxed in methanol with concentrated sulfuric acid as the catalyst to provide methyl 4,4-bis(4-hydroxyphenyl)valerate (VIII). Methyl 4,4-bis(4-hydroxylphenyl)valerate (IX) is reacted with 1,1,1,3,3,3-hexamethyldisilazane (HMDS) and chlorotrimethylsilane (TMSCl), then reduced by lithium aluminum hydride (LiAlH$_4$) to provide 4,4-bis(4-hydroxyphenyl)valeric alcohol (VIII). 4,4-Bis(4-hydroxyphenyl)valeric alcohol (VIII) is reacted with dihydropyran (DHP) to produce the desired monomer, THP protected 4,4-bis(4-hydroxyphenyl)valeric alcohol (VI).

added a dichloromethane solution containing a bischloroformate, such as 4,4-cyclohexylidenebisphenol bischloroformate. A catalyst, such as triethylamine, tributylamine or the like, can be added to further accelerate the reaction. The interfacial polycondensation is generally accomplished by heating at a temperature of from 0° C. to about 100° C., and preferably from room temperature (25° C.) to about 50° C.; the reaction time is generally from about 10 minutes to about 3 hours. The polymeric product obtained can be purified by dissolving it in an organic solvent, such as dichloromethane or tetrahydrofuran (THF), and then precipitating in methanol. Product structures can be confirmed by NMR and IR spectroscopy. The number and weight average molecular weights of the polymer and the $M_w/M_n$ can be obtained by a Waters Gel Permeation Chromatograph (GPC) employing four ULTRASTYRAGEL® columns with pore sizes of 100, 500, 500, and 104 Angstroms and using THF as a solvent.

The THP-protected hydroxyl polycarbonate obtained was stirred and heated with an acid or a salt, such as hydrochloric

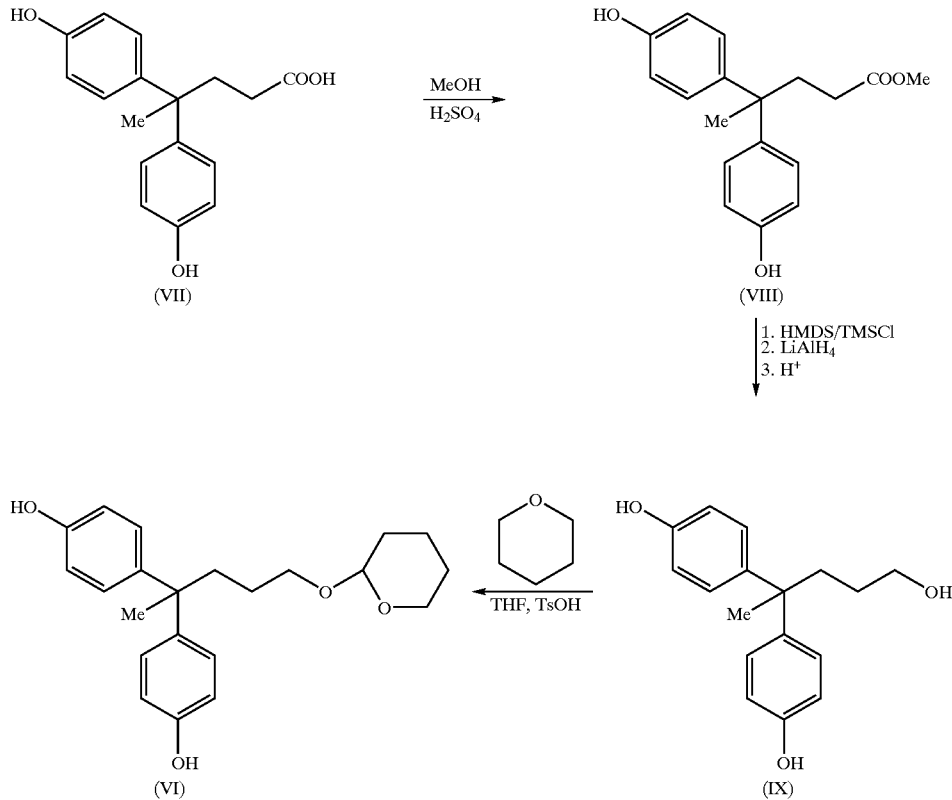

Scheme (III)

More specifically, the hydroxy-pendent polycarbonates (II) can be prepared by the following method. A mixture of THP-protected 4,4-bis(4-hydroxyphenyl)valeric alcohol (VI) and optionally other bisphenol monomers, such as 4,4-cyclohexylidenebisphenol, an aqueous inorganic base solution, such as sodium hydroxide, and an organic solvent, such as dichloromethane, a suitable amount of a phase transfer catalyst, such as benzyltriethylammonium chloride, is stirred at room temperature (25° C.). To the mixture is acid, toluenesulfonic acid, pyridinium toluenesulfonate and the like, and alcohol, such as methanol, ethanol, propanol and the like, in an organic solvent, such as methylenechloride, tetrahydrofuran or the like. The temperature was controlled at from about 30° C. to about 100° C., and preferably, from about 40° C. to about 70° C.; reaction time is, for example, for about 6 to about 72 hours, and preferably for about 12 to about 24 hours. The completion of the reaction was monitored by the disappearance of the singlet at δ 4.5 ppm on the ¹H NMR spectrum, and the resulting hydroxyl polycarbonate was precipitated into methanol, collected by filtration and dried at 70° C. under vacuum. The number and weight molecular weight of the resulting hydroxyl polycarbonate can be obtained by GPC to determine if there has been a change in the molecular weight of the product after converting from the THP-protected hydroxyl polycarbonate to a hydroxyl polycarbonate.

The substrate layers selected for the imaging members of the present invention can be opaque or substantially transparent, and may comprise any suitable material having the requisite mechanical properties. Thus, the substrate may comprise a layer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate may be flexible, seamless, or rigid, and may have a number of many different configurations, such as for example a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer may be of substantial thickness, for example in excess of about 3,000 microns, or of a minimum thickness. In embodiments, the thickness of this layer is from about 75 microns to about 300 microns, and more specifically, from about 70 to about 150 microns.

The photogenerating layer can contain known photogenerating pigments, such as metal phthalocyanines, metal free phthalocyanines, hydroxygallium phthalocyanines, perylenes, especially bis(benzimidazo)perylene, titanyl phthalocyanines, and the like, and more specifically, vanadyl phthalocyanines, Type V hydroxygallium phthalocyanines, and inorganic components, such as selenium, especially trigonal selenium. The photogenerating pigment can be dispersed in a resin binder or alternatively no resin binder is needed. Generally, the thickness of the photogenerator layer depends on a number of factors, including the thicknesses of the other layers and the amount of photogenerator material contained in the photogenerating layers. Accordingly, this layer can be of a thickness of, for example, from about 0.05 micron to about 10 microns, and more specifically, from about 0.25 micron to about 3 microns when, for example, the photogenerator compositions are present in an amount of from about 30 to about 75 percent by volume. The maximum thickness of the layer in an embodiment is dependent primarily upon factors, such as photosensitivity, electrical properties and mechanical considerations. The photogenerating layer binder resin, present in various suitable amounts, for example from about 1 to about 50, and more specifically, from about 1 to about 10 weight percent, may be selected from a number of known polymers, such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. In embodiments of the present invention, it is desirable to select a coating solvent that does not substantially disturb or adversely effect the other previously coated layers of the device. Examples of solvents that can be selected for use as coating solvents for the photogenerator layer are ketones, alcohols, aromatic hydrocarbons, halogenated aliphatic hydrocarbons, ethers, amines, amides, esters, and the like. Specific examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethyl formamide, dimethyl acetamide, butyl acetate, ethyl acetate, methoxyethyl acetate, and the like.

The coating of the photogenerator layers in embodiments of the present invention can be accomplished with spray, dip or wire-bar methods such that the final dry thickness of the photogenerator layer is, for example, from about 0.01 to about 30 microns, and more specifically, from about 0.1 to about 3 microns after being dried at, for example, about 40° C. to about 150° C. for about 15 to about 90 minutes.

Illustrative examples of polymeric binder materials that can be selected for the photogenerator layer are as indicated herein, and include those polymers as disclosed in U.S. Pat. No. 3,121,006, the disclosure of which is totally incorporated herein by reference. In general, the effective amount of polymer binder that is utilized in the photogenerator layer is from about 0 to about 95 percent by weight, and preferably from about 25 to about 60 percent by weight of the photogenerator layer.

As optional adhesives usually in contact with the supporting substrate layer, there can be selected various known substances inclusive of polyesters, polyamides, poly(vinyl butyral), poly(vinyl alcohol), polyurethane and polyacrylonitrile. This layer is, for example, of a thickness of from about 0.001 micron to about 1 micron. Optionally, this layer may contain effective suitable amounts, for example from about 1 to about 10 weight percent, of conductive and nonconductive particles, such as zinc oxide, titanium dioxide, silicon nitride, carbon black, and the like, to provide, for example, in embodiments of the present invention desirable electrical and optical properties.

The charge transport layer can be comprised of known hole transports, such as aryl amines, and which generally is of a thickness of from about 5 microns to about 80 microns, and preferably is of a thickness of from about 10 microns to about 44 microns, and which aryl amines include molecules of the following formula

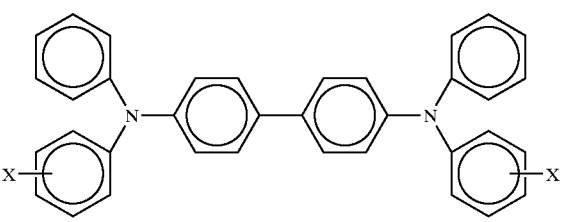

wherein X is an alkyl group, a halogen, or mixtures thereof, especially those substituents selected from the group consisting of Cl and CH₃.

Examples of specific aryl amines are N,N'-diphenyl-N, N'-bis(alkylphenyl)-1,1-biphenyl-4,4'-diamine wherein alkyl is selected from the group consisting of methyl, ethyl, propyl, butyl, hexyl, and the like; and N,N'-diphenyl-N,N'-bis(halophenyl)-1,1'-biphenyl-4,4'-diamine wherein the halo substituent is preferably a chloro substituent. Other known charge transport layer molecules can be selected, reference for example U.S. Pat. Nos. 4,921,773 and 4,464,450, the disclosures of which are totally incorporated herein by reference.

Generally, the transport layer contains from about 10 to about 75 percent by weight of the charge transport material, and more specifically, from about 35 percent to about 50 percent of this material.

Also, included within the scope of the present invention are methods of imaging and printing with the photoresponsive devices illustrated herein. These methods generally involve the formation of an electrostatic latent image on the imaging member, followed by developing the image with a toner composition comprised, for example, of thermoplastic resin, colorant, such as pigment, charge additive, and surface additives, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The following Examples are being submitted to illustrate specific embodiments of the present invention. These Examples are intended to be illustrative only and are not intended to limit the scope of the present invention. Also, parts and percentages are by weight unless otherwise indicated.

EXAMPLE I

Synthesis of Methyl 4,4-bis(4-hydroxyphenyl)valerate (VIII):

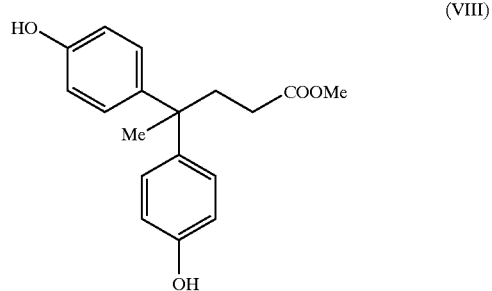

(VIII)

4,4'-Bis(4-hydroxyphenol)valeric acid (VII) (28.6 grams, 0.1 mol) was dissolved in 120 milliliters of methanol in a 250 milliliters round-bottomed flask equipped with a condenser, followed by the addition of 3 grams (0.03 mol, 0.3 equiv.) of sulfuric acid. The mixture was heated at reflux for 4 hours. After the aforementioned esterification was complete, the reaction mixture was cooled to room temperature, about 25° C., then poured over ice. The mixture was stirred and washed with water. The resulting separated solid was subjected to grinding and washed with sodium bicarbonate to pH 7. The resulting solid was collected by filtration and recrystallized from hot, about 60° C., water and methanol to produce white iridescent crystals. The ester product was dried under high vacuum at 60° C. overnight, about 18 hours, resulting in 27.7 grams (92.2 percent) of (VIII) as confirmed by $^1$H NMR.

EXAMPLE II

Synthesis of 4,4-Bis(4-hydroxyphenyl)valeric Alcohol (IX):

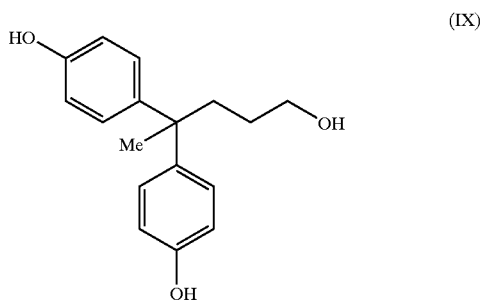

(IX)

Methyl 4,4-bis(4-hydroxyphenyl)valerate (VIII) of Example I (16.2 grams, 54 mmol) was placed in a 250 milliliters round-bottomed flask equipped with a condenser. 1,1,1,3,3,3-Hexamethyldisilazane (HMDS) (21 milliliters) and chlorotrimethylsilane (TMSCl) (0.8 milliliter) were added to the flask under argon. The mixture was heated at reflux for 5 hours, cooled and evaporated to dryness under a high vacuum. The residue was dissolved in 24 milliliters of THF. To a 500 milliliter 3-neck round-bottomed flask equipped with a condenser under argon containing 81 milliliters of dry THF, were slowly added 2.756 grams of LiAlH$_4$. The THF solution was then added gradually to the LiAlH$_4$/THF mixture and heated to reflux for 4 hours. The mixture was cooled, and 15 percent w/w aqueous ammonium chloride and concentrated HCl were added to arrive at a pH of 2. The mixture was filtered and the filtrate was collected, which was concentrated and dried under high vacuum at room temperature overnight, about 20 hours, to provide the above product 14.08 grams (95.6 percent); confirmed by $^1$H NMR.

EXAMPLE III

Synthesis of Tetrahydropyranyl-protected 4,4-bis(4-hydroxyphenyl)valeric Alcohol (VI):

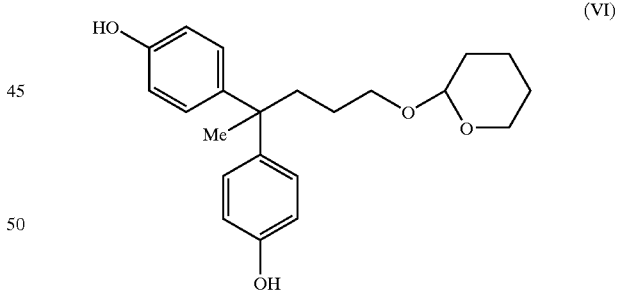

(VI)

A mixture of 4,4-bis(4-hydroxyphenyl)valeric alcohol (IX) of Example II (34.7 grams), p-toluenesulfonic acid monohydrate (0.2426 gram) and 300 milliliters of THF were added to a 500 milliliter round-bottomed flask equipped with a condenser under argon and heated to 56° C. until well mixed. 10.713 Grams of 3,4-dihydro-2H-pyran (127 mmol) were slowly added with thorough mixing between additions and stirred overnight, about 18 to about 20 hours throughout. When the reaction was complete, the mixture was evaporated to dryness and separated by flash chromatography eluting with 5:1 hexane/acetone gradually decreasing (3.5:1, 2:1) to pure acetone. The desired fractions were concentrated and dried overnight under high vacuum to provide the above product, tetrahydropyranyl protected 4,4-bis(4-hydroxyphenyl)valeric alcohol (VI), as a yellow oil; 24.9 grams (54.8 percent). The product was recrystallized from cold, below about room temperature, $CH_2Cl_2$ or acetone/hexane to provide a white powder, 15.09 grams (33.2 percent yield); mp 131° C. (DSC); structure of (VI) confirmed by $^1H$ NMR.

EXAMPLE IV liliters of $CH_2Cl_2$ in a 50 milliliter round-bottom flask, then slowly added to a rapidly stirring above mixture. The reaction was continued at room temperature for 3 hours. The resulting viscous solution was diluted with $CH_2Cl_2$ (100 milliliters) and deionized water (100 milliliters). The organic layer formed was separated and washed with deionized water then dropped into methanol. The resulting polymer was collected by filtration. After drying under high vacuum at 70° C. overnight, the above protected hydroxy- Synthesis of Tetrahydropyranyl Protected Hydroxyl Polycarbonate(III-Pa; x = 0.05, y = 0.95):

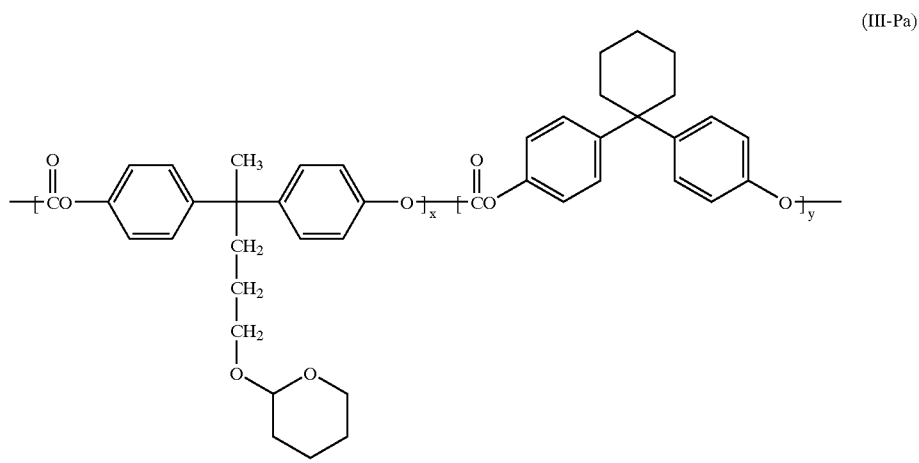

In a 500 milliliter Erlenmeyer flask was added a 4 percent w/w aqueous sodium hydroxide solution (100 grams), 4,4'-cyclohexylidene bisphenol (5.367 grams), THP-protected 4,4-bis(4-hydroxyphenyl)valeric alcohol (V) (0.8912 gram) prepared above, benzyltriethylammonium chloride (0.1139 gram), 50 milliliters of $CH_2Cl_2$ and tributylamine (0.1 gram). The mixture was stirred vigorously at room temperature, about 23° C., to about 25° C. Bisphenol Z bischloroformate (10.819 grams) was dissolved in 50 milpolycarbonate (III-Pa) was obtained as white fibers: 14.31 grams (95.7 percent); $M_n$=56,000, $M_w$=114,000.

EXAMPLE V

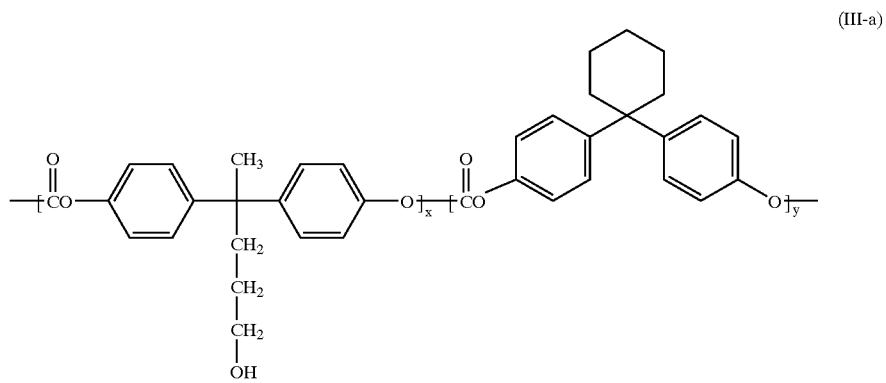

In a 1,000 milliliter round-bottomed flask, the protected hydroxyl polycarbonate (II-Pa) (12.268 grams) prepared above was dissolved in $CH_2Cl_2$ (120 milliliters). Methanol (24 milliliters) was then added to the reaction mixture. To the rapidly stirring mixture was added 0.24 gram of pyridinium p-toluenesulfonate followed by heating to reflux under argon (60° C.) for 24 to 72 hours. The completion of the reaction was monitored by the disappearance of the singlet at δ 4.5 ppm on the $^1$H NMR spectrum. The polymer was precipitated into methanol and collected by filtration. After drying under high vacuum at 70° C. overnight, the hydroxy-polycarbonate (IIIa) was obtained as white flakes: 11.59 grams (95.8 percent yield throughout); $M_n$=49,000, $M_w$=89,000.

EXAMPLE VI

Synthesis of Hydroxyl Polycarbonate (III-Pa; x=0.10, y=0.90)

In a 500 milliliter Erlenmeyer flask was added a 4 percent w/w of an aqueous sodium hydroxide solution (100 grams), 4,4-cyclohexylidenebisphenol (4.6964 grams), tetrahydropyranyl-protected 4,4-bis(4-hydroxyphenyl) valeric alcohol prepared above (1.7828 grams), benzyltri-ethylammonium chloride (0.1139 gram), and 50 milliliters of $CH_2Cl_2$ and tributylamine (0.1 gram). The mixture was stirred vigorously at room temperature. Bisphenol Z bis-chloroformate (10.8170 grams) was dissolved in 50 milliliters of $CH_2Cl_2$ in a 50 milliliter round-bottom flask, then slowly added to the rapidly stirred above mixture. The reaction was completed at room temperature for 3 hours, and the viscous solution resulting was diluted with $CH_2Cl_2$ (100 milliliters) and deionized water (100 milliliters). The organic layer formed was separated and washed with deionized water thoroughly then dropped into methanol. The resulting polymer was collected by filtration. After drying under high vacuum at 70° C. overnight, the protected hydroxy-polycarbonate (III-Pa) was obtained as white fibers: 15.28 Grams (94.1 percent); $M_n$=46,000, $M_w$=89,500.

EXAMPLE VIII

Synthesis of Hydroxyl Polycarbonate (IIIa; x=0.10, y=0.90)

In a 1,000 milliliter round-bottomed flask, the protected PC-OH (II-Pa; x=0.10, y=0.90) (12.268 grams) was dissolved in $CH_2Cl_2$ (120 milliliters). Methanol (24 milliliters) was then added to the reaction mixture. To the rapidly stirring mixture was added 0.24 gram of pyridinium p-toluenesulfonate and the mixture was then heated to reflux under argon (60° C.) for 24 to 72 hours. The completion of the reaction was monitored by the disappearance of the singlet at δ 4.5 ppm on the $^1$H NMR spectrum, and the polymer resulting was precipitated into methanol and collected by filtration. After drying under high vacuum at 70° C. overnight the hydroxy-polycarbonate (IIIa; x=0.10, y=0.90) was obtained as white flakes: 11.59 grams (95.8 percent); $M_n$=49,000, $M_w$=89,000.

The polycarbonates generated in the above Examples can be selected for photoconductive imaging members, reference for example U.S. Serial No. (not yet assigned-D/A1261) and U.S. Serial No. (not yet assigned-D/A2340), the disclosures of which are totally incorporated herein by reference.

EXAMPLE VIII

A photoresponsive imaging device was fabricated as follows.

On a 75 micron thick titanized MYLAR® substrate was coated by draw bar techniques a barrier layer formed from hydrolyzed gamma aminopropyltriethoxysilane and which ayer is of a thickness of 0.005 micron. The barrier layer coating composition was prepared by mixing 3-aminopropyltriethoxysilane with ethanol in a 1:50 volume 1 ratio. The coating was allowed to dry for 5 minutes at room temperature, followed by curing for 10 minutes at 110° C. in a forced air oven. On top of the barrier/blocking layer was coated a 0.05 micron thick adhesive layer prepared from a solution of 2 weight percent of an E.I DuPont 49K (49,000) polyester in dichloromethane. A 0.2 micron photogenerating layer was then coated on top of the adhesive layer from a dispersion of hydroxy gallium phthalocyanine Type V (0.46 gram) and a polystyrene-b-polyvinylpyridine block copolymer binder (0.48 gram) in 20 grams of toluene, followed by drying at 100° C. for 10 minutes. Subsequently, a 25 micron hold transport layer (CTL) was coated on top of the photogenerating layer from a solution of N,N'-diphenyl-N,N-bis (3-methylphenyl)-1,1'-biphenyl-4,4'-diamine (2.64 grams), the hydroxyl polycarbonate of Formula IIa (3.5 grams) prepared in Example V and 1,6-hexyldiisocyanate (0.2 gram) in 40 grams of dichloromethane. After coating, the resulting device was dried and cured at 135° C. for 15 minutes to provide an imaging member that exhibited excellent resistance, that is no adverse effects or dissolving, to common organic solvents, such as, for example, methylenechloride, methanol, ethanol and the like, and which device was robust and abrasion resistant as determined by an abrasion test with toner particles.

The xerographic electrical properties of the imaging members can be determined by known means, including as indicated herein electrostatically charging the surfaces thereof with a corona discharge source until the surface potentials, as measured by a capacitively coupled probe attached to an electrometer, attained an initial value $V_o$ of about −800 volts. After resting for 0.5 second in the dark, the charged members attained a surface potential of $V_{ddp}$, dark development potential. Each member was then exposed to light from a filtered Xenon lamp with a XBO 150 watt bulb, thereby inducing a photodischarge which resulted in a reduction of surface potential to a $V_{bg}$ value, background potential. The percent of photodischarge was calculated as $100 \times (V_{ddp}-V_{bg})/V_{ddp}$. The desired wavelength and energy of the exposed light was determined by the type of filters placed in front of the lamp. The monochromatic light photosensitivity was determined using a narrow band-pass filter.

An illustrative wear test on the drum photoreceptor device of the present invention was accomplished as follows.

Photoreceptor wear was determined by the difference in the thickness of photoreceptor before and after the wear test. For the thickness measurement, the photoreceptor was mounted onto the sample holder to zero the permascope at the uncoated edge of the photoreceptor; the thickness was measured at one-inch intervals from the top edge of the coating along its length using a permascope, ECT-100, to obtain an average thickness value.

The following table summarizes the electrical and the wear test performance of these devices wherein CTL represents the charge transport layers, and PCZ represents a known polycarbonate; the lower the number, the better the wear rate.

| DEVICE | Vddp (-kV) | E½ (Ergs/cm)2 | Dark Decay (V @ 500 ms) | Vr (V) | Wear (nm/k cycles) |
|---|---|---|---|---|---|
| Control Device with PCZ as CTL Binder | 4.87 | 1.11 | 10.3 | 15 | 50.0 |
| Device with Crosslinked CTL [Hydroxyl Polycarbonate and HDI] | 4.84 | 1.33 | 9.5 | 44 | 31.9 |

EXAMPLE IX

A photoresponsive imaging device incorporating into the charge transport layer the hydroxyl polycarbonate (IIa) (3.5 grams) of Example V with 1,6-hexyldiisocyanate (0.4 gram) as the crosslinked polycarbonate binder was prepared in accordance with the procedure of Example VIII. The following table summarizes the electrical characterizations and the wear test performance of this device.

| DEVICE | Vddp (V) | E½ (Ergs/cm)2 | Dark Decay (V @ 500 ms) | Vr (V) | Wear (nm/k cycles) |
|---|---|---|---|---|---|
| Control Device with PCZ as CTL binder | 4.87 | 1.11 | 10.3 | 15 | 50.0 |
| Device with crosslinked CTL [hydroxyl polycarbonate and HDI] | 4.87 | 1.25 | 9.0 | 49 | 35.7 |

EXAMPLE X

A photoresponsive imaging device incorporating into the charge transport layer the hydroxyl polycarbonate (IIIa) (3.5 grams) of Example VII with 1,6-hexyldiisocyanate (0.8 gram) as the crosslinked polycarbonate binder was prepared in accordance with the procedure of Example VIII. The following table summarizes the electrical characteristics and the wear test performance of this device.

| DEVICE | Vddp (V) | E½ (Ergs/cm)2 | Dark DeCay (V @ 500 ms) | Vr (V) | Wear (nm/k cycles) |
|---|---|---|---|---|---|
| Control Device with PCZ as CTL Binder | 4.87 | 1.11 | 10.3 | 15 | 50.0 |
| Device with Crosslinked CTL [Hydroxyl Polycarbonate and HDI] | 4.87 | 1.30 | 9.5 | 47 | 25.1 |

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A polycarbonate comprised of a repeating segment represented by Formula (I)

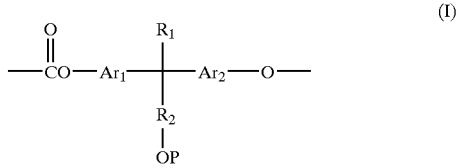

(I)

wherein $R_1$ is selected from the group consisting of hydrogen, alkyl, and aryl; $R_2$ represents a divalent linkage selected from the group consisting of alkylene optionally containing one or more heteroatoms of halogen, nitrogen, oxygen, sulfur, silicon, or phosphorus, arylalkylene, and arylene; $Ar_1$ and $Ar_2$ each independently represent aromatic groups; and P represents a hydrogen atom, or a hydroxyl protective group.

2. A polycarbonate in accordance with claim 1 wherein $R_1$ is an alkyl group containing from about 1 to about 15 carbon atoms.

3. A polycarbonate in accordance with claim 1 wherein said alkyl for $R_1$ is methyl, ethyl, propyl, butyl, pentyl, or hexyl.

4. A polycarbonate in accordance with claim 1 wherein said $R_1$ alkyl is a halogenated alkyl of fluoroalkyl, perfluoroalkyl, or chloroalkyl, and wherein said alkyl contains from 1 to about 15 carbons.

5. A polycarbonate in accordance with claim 1 wherein $R_2$ alkylene contains from 1 to about 15 carbons.

6. A polycarbonate in accordance with claim 1 wherein $R_2$ is selected from the group consisting of dimethylene, trimethylene, and tetramethylene.

7. A polycarbonate in accordance with claim 1 wherein each of $Ar_1$ and $Ar_2$ are arylene containing from about 6 to about 30 carbon atoms.

8. A polycarbonate in accordance with claim 7 wherein said arylene is selected from the group consisting of

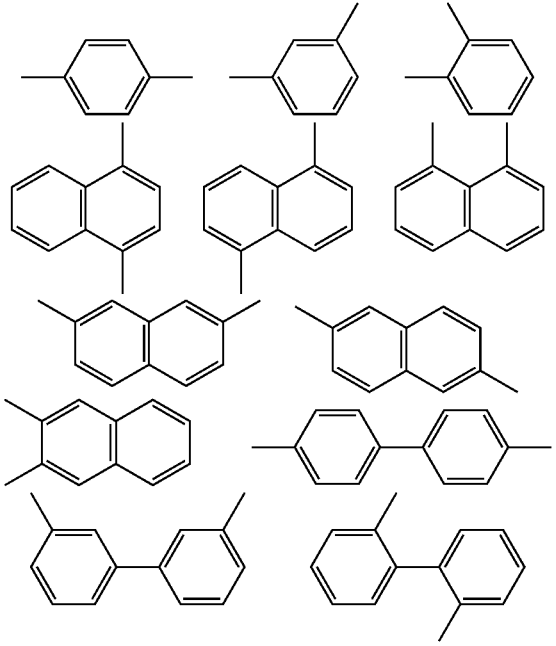

and wherein said arylene optionally contains a substituent selected from the group consisting of hydrogen, halogen, alkyl of from 1 to about 15 carbon atoms, halogenated alkyl of 1 to about 15 carbons, or alkyl containing one or more heteroatoms of nitrogen, oxygen, sulfur, silicon, or phosphorus.

9. A polycarbonate in accordance with claim 1 wherein P is a hydrogen atom.

10. A polycarbonate in accordance with claim 1 wherein P is selected from the group comprised of a pyranyl, a thiopyranyl, an alkoxyalkyl, an alkylsilyl, an alkylarylsilyl, an acyl, and a benzyl.

11. A polycarbonate in accordance with claim 1 wherein said P is selected from the group comprised of tetrahydropyranyl, 4-methoxytetrahydropyranyl, tetrahydrofuranyl, 1-ethoxyethyl, acetyl, tert-butyldimethylsilyl, and benzyl.

12. A polycarbonate composed in accordance with claim 1 further containing at least one repeating segment represented by Formula (II)

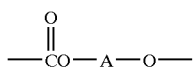
(II)

wherein A is a divalent hydrocarbon optionally containing from about 2 to about 30 carbon atoms, or optionally a divalent hydrocarbon linkage containing from about 2 to about 30 carbon atoms further containing a heteroatom of oxygen, nitrogen, sulfur, silicon, or phosphorus and wherein $R_1$ is selected from the group consisting of hydrogen, alkyl, and aryl.

13. A polycarbonate in accordance with claim 12 wherein A is selected from the group comprised of

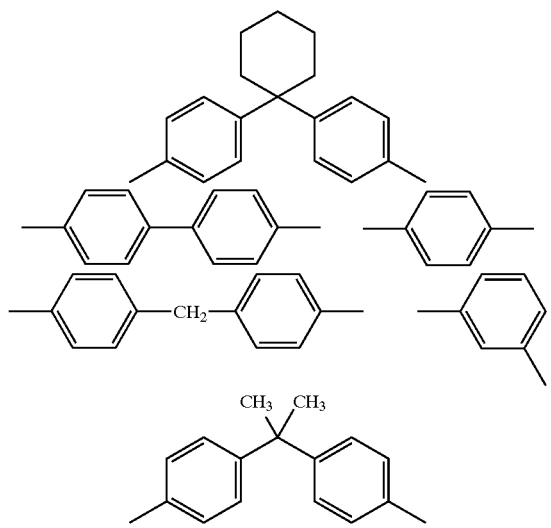

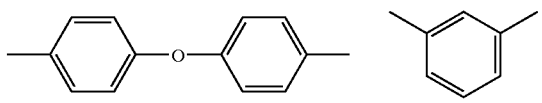

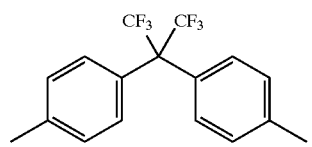

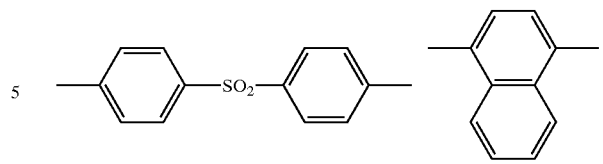

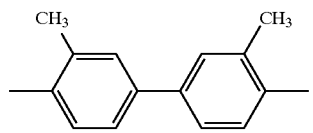

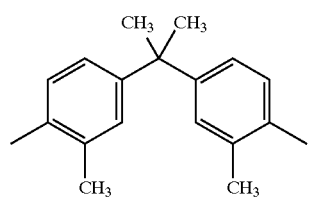

—CH$_2$CH$_2$— —CH$_2$CH$_2$CH$_2$CH$_2$— —CH$_2$CH$_2$OCH$_2$CH$_2$—·

14. A polycarbonate in accordance with claim 12 wherein the polycarbonate is represented by the general Formula (III)

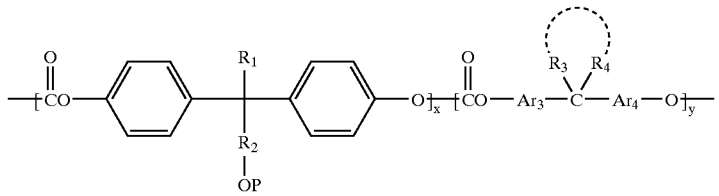

(III)

wherein $R_1$ is selected from the group consisting of hydrogen, alkyl of from about 1 to about 15 carbon atoms, a halogenated alkyl of from about 1 to about 15 carbon atoms, an alkyl of from about 1 to about 15 carbon atoms further containing one or more heteroatoms selected from the group consisting of nitrogen, oxygen, sulfur, silicon, and phosphorus, and an aryl or substituted aryl of from about 6 to about 30 carbons; $R_2$ represents a divalent linkage selected from the group consisting of an alkylene containing from about 1 to about 15 carbon atoms; P represents a hydrogen atom, or a hydroxyl protective group; $Ar_3$ and $Ar_4$ each independently represent aromatic groups of from about 6 to about 30 carbon atoms; $R_3$ and $R_4$ are independently selected from the group consisting of hydrogen, alkyl of from about 1 to about 15 carbon atoms, and aryl or substituted aryl of from about 6 to about 30 carbon atoms; wherein $R_3$ and $R_4$ may form a combined ring structure containing from about 5 to about 20 carbon atoms; and wherein x and y are the mole fractions of the repeating units such that x+y is equal to 1.

15. A polycarbonate in accordance with claim 14 wherein said alkyl for $R_1$ is selected from a group consisting of methyl, ethyl, propyl, butyl, pentyl, and hexyl.

16. A polycarbonate in accordance with claim 14 wherein said halogenated alkyl for $R_1$ is a fluoroalkyl, perfluoroalkyl, or a chloroalkyl, and wherein said alkyl contains from 1 to about 10 carbon atoms.

17. A polycarbonate in accordance with claim 14 wherein $R_2$ is an alkylene with from 2 to about 12 carbon atoms.

18. A polycarbonate in accordance with claim 14 wherein $R_2$ is selected from the group consisting of dimethylene, trimethylene, and tetramethylene.

19. A polycarbonate in accordance with claim 14 wherein each of $Ar_3$ and $Ar_4$ are arylene groups containing from about 6 to about 30 carbon atoms.

20. A polycarbonate in accordance with claim 19 wherein said arylene group is selected from the group comprised of

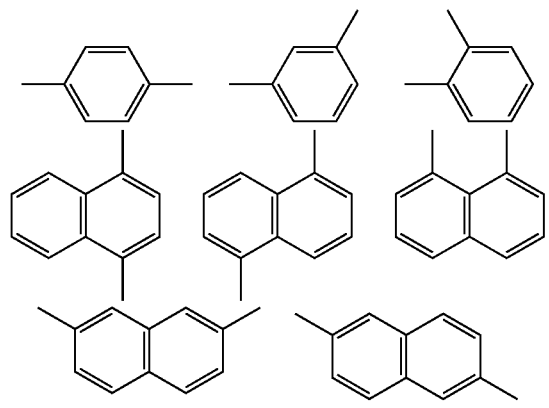

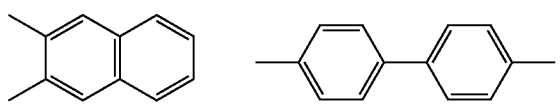

-continued

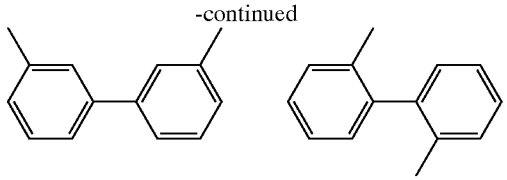

and wherein said arylene group optionally contains a substituent selected from the group consisting of hydrogen, halogen, alkyl containing from 1 to about 15 carbon atoms, halogenated alkyl of 1 to about 15 carbon atoms, and alkyl containing one or more heteroatoms of nitrogen, oxygen, sulfur, silicon, or phosphorus.

21. A polycarbonate in accordance with claim 14 wherein P is a hydrogen atom.

22. A polycarbonate in accordance with claim 14 wherein P is selected from the group consisting of a pyranyl, a thiopyranyl, an alkoxyalkyl, an alkylsilyl, an alkylarylsilyl, an acyl, and a benzyl.

23. A polycarbonate in accordance with claim 14 wherein said P is selected from the group consisting of tetrahydropyranyl, 4-methoxytetrahydropyranyl, tetrahydrofuranyl, 1-ethoxyethyl, acetyl, and tert-butyldimethylsilyl.

24. A polycarbonate in accordance with claim 14 wherein $R_3$ and $R_4$ each are independently selected from the group consisting of an alkyl group of from about 1 to about 15 carbon atoms, or a halogenated alkyl group of from about 1 to about 15 carbon atoms.

25. A polycarbonate in accordance with claim 14 wherein said alkyl group is selected from the group consisting of trifluoromethyl, and 3,3,3-trifluoropropyl.

26. A polycarbonate in accordance with claim 14 wherein $R_3$ and $R_4$ form a combined structure of about 5 to about 10 carbon atoms.

27. A polycarbonate in accordance with claim 14 wherein $R_1$ is a methyl; $R_2$ is a trimethylene, and P is a hydrogen atom.

28. A polycarbonate in accordance with claim 14 wherein said polycarbonate possesses a weight average molecular weight of from about 2,000 to about 500,000.

29. A polycarbonate in accordance with claim 14 and wherein said polycarbonate is comprised of

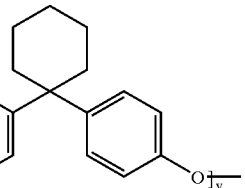

(III-a)

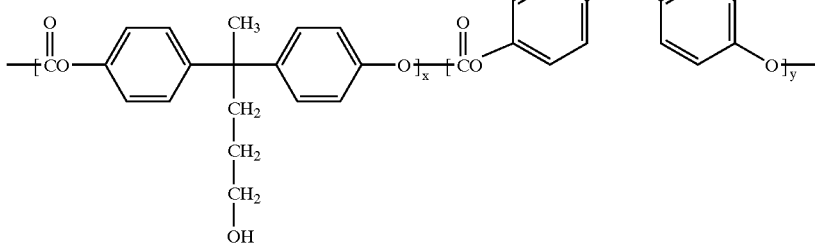

wherein x and y represent mole fractions such that x+y is equal to 1, and wherein said polycarbonate possesses a weight $M_w$ average molecular weight of from about 2,000 to about 500,000.

30. A monomer comprised of

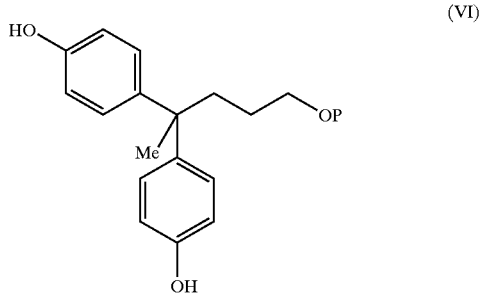

(VI)

wherein P is a protective group selected from the group consisting of a pyranyl, a thiopyranyl, an alkoxyalkyl, an alkylsilyl, an alkylarylsilyl, an acyl, and a benzyl.

31. A polycarbonate in accordance with claim 14 and which polycarbonate is crosslinked and is formed from the reaction of a diisocyanate and a polymer comprised of Formula (III)

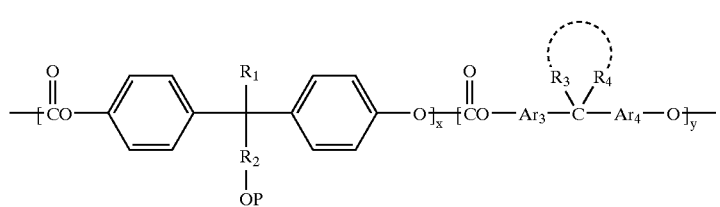

(III)

wherein P is hydrogen; $R_1$ is selected from the group consisting of hydrogen, alkyl containing from about 1 to about 15 carbon atoms, a halogenated alkyl containing from about 1 to about 15 carbon atoms, an alkyl of from about 1 to about 15 carbon atoms optionally further containing one or more heteroatoms selected from the group consisting of nitrogen, oxygen, sulfur, silicon, and phosphorus, an aryl or substituted aryl of from about 6 to about 30 carbons; $R_2$ represents a divalent linkage selected from the group consisting of an alkylene containing from about 1 to about 15 carbon atoms, $Ar_3$ and $Ar_4$ each independently represent aromatic groups containing from about 6 to about 30 carbon atoms; $R_3$ and $R_4$ are independently selected from the group consisting of hydrogen, alkyl of from about 1 to about 15 carbon atoms, and aryl or substituted aryl of from about 6 to about 30 carbon atoms; and optionally wherein $R_3$ and $R_4$ may form a combined ring structure containing from about 5 to about 20 carbon atoms; wherein x and y represent the mole fractions of the repeating segments such that x+y is equal to 1; and wherein x is from about 0.03 to about 1, and y is from about 0.07 to about 1.

32. A crosslinked polycarbonate in accordance with claim 31, wherein said diisocyanate is selected from the group comprising 1,6-diisocyanatohexane, 1,8-diisocyanatooctane, 1,3-bis(isocyanatomethyl)cyclohexane, 4,4'-ethylenebis(cyclohexylisocyanate), phenylisocyanate, 1,3-bis(isocyanatomethyl)-benzene, 1,4-phenylenediisocyanate, and toluene 2,4-diisocyanate.

33. A crosslinked polycarbonate in accordance with claim 31 formed by reaction of said polycarbonate and said diisocyanate at from about 25° C. to about 250° C. wherein said reaction is catalyzed by a tertiary amine or a metal compound.

34. A crosslinked polycarbonate in accordance with claim 33 wherein said catalyst is triethylamine, tributylamine, dibutyltin diacetate, dibutyltin dilaurate, bis(trioctyltin) oxide, zinc octate, or zinc bis(2-ethylhexanoate).

35. A polycarbonate in accordance with claim 1 wherein $R_1$ alkyl contains from about 1 to about 15 carbon atoms; $R_1$ is a halogenated alkyl containing from about 1 to about 15 carbon atoms; said $R_1$ alkyl contains from about 2 to about 12 carbon atoms further containing one or more heteroatoms selected from the group consisting of nitrogen, oxygen, sulfur, silicon, and phosphorus, an aryl or substituted aryl of from about 6 to about 30 carbons; said $R_2$ divalent linkage is selected from the group consisting of an alkylene of from about 2 to about 12 carbon atoms; $Ar_1$ and $Ar_2$ each independently represent aryl containing from about 6 to about 30 carbon atoms, and wherein the repeating segment of Formula I represents a number of from about 5 to about 500.

36. A polycarbonate in accordance with claim 1 wherein said repeating segment is

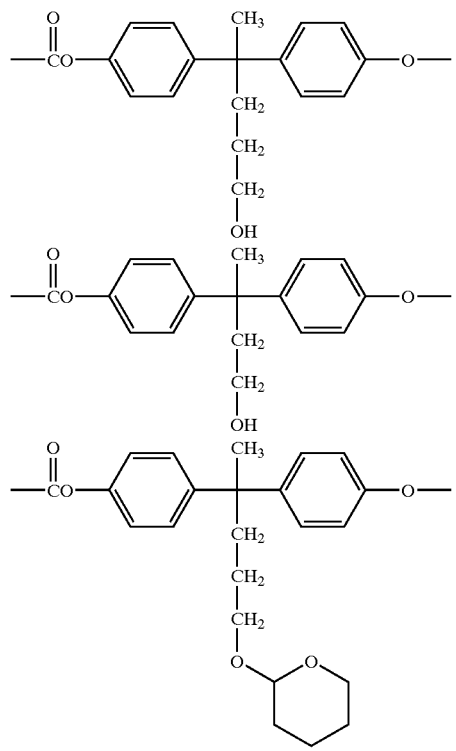

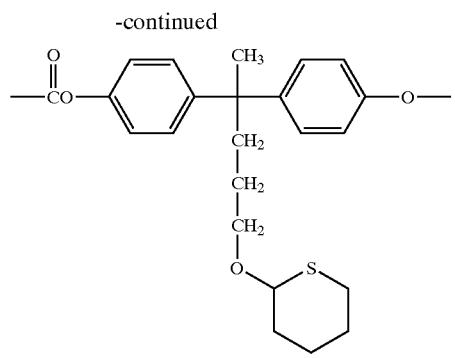
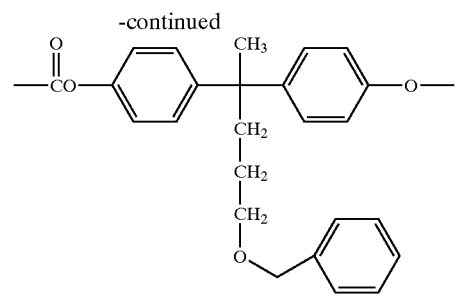
37. A crosslinked polycarbonate in accordance with claim 31 wherein said polymer is alternatively
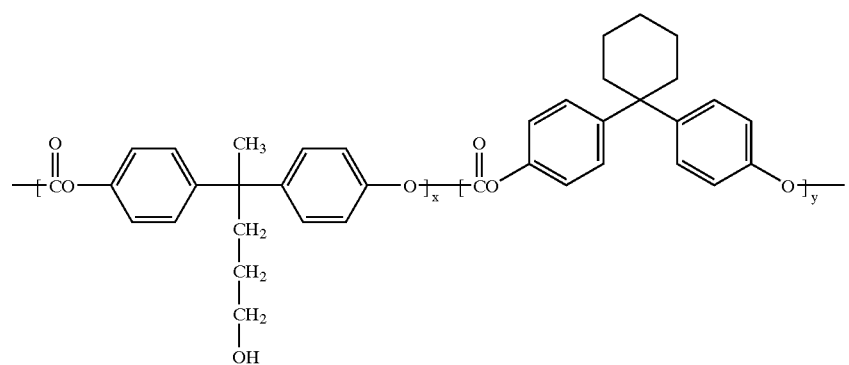
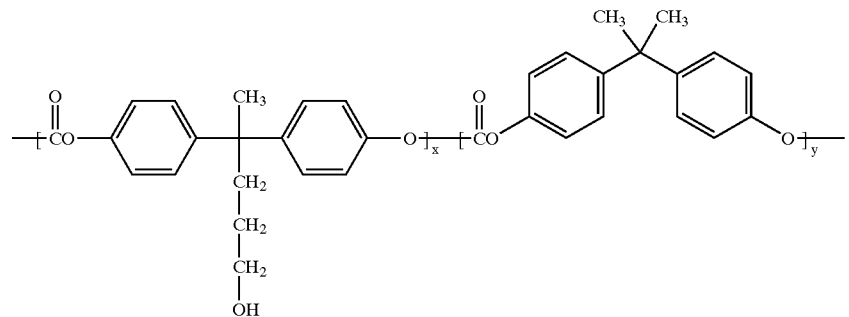
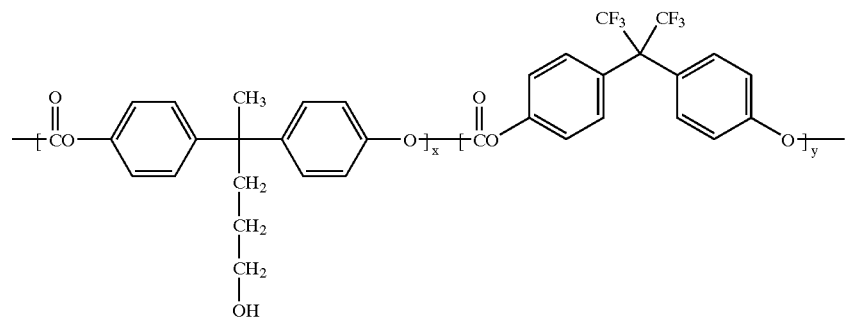

-continued

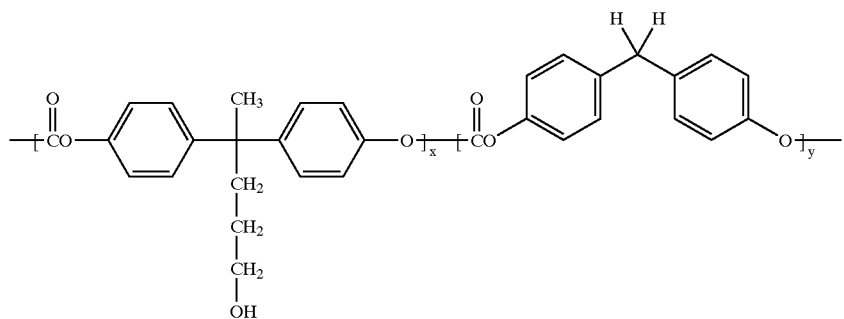

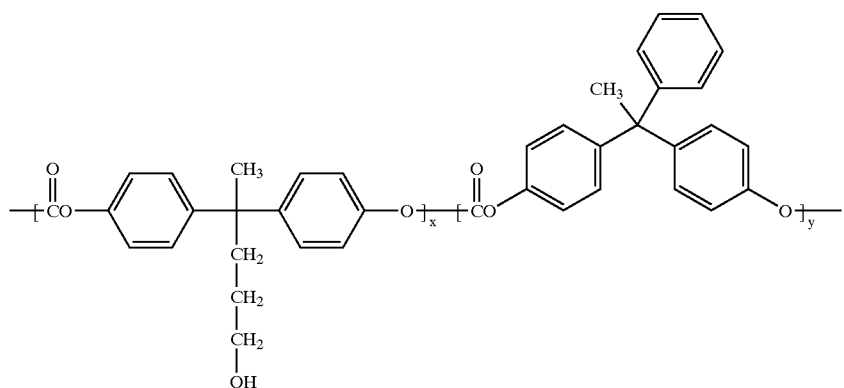

38. A polycarbonate in accordance with claim 1 and containing a repeating segment represented by Formula (I)

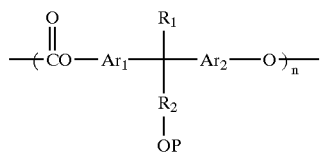

(I)

wherein $R_1$ is selected from the group comprised of hydrogen, alkyl, and aryl; $R_2$ represents a divalent linkage selected from the group comprised of alkylene, and arylene; $Ar_1$ and $Ar_2$ are each independently aryl; P represents a hydrogen atom, or a hydroxyl protective group, and wherein n represents the number of segments with the number being from about 5 to about 1,000.

39. A polycarbonate in accordance with claim 38 wherein n is from about 10 to about 500; wherein alkyl is halogenated alkyl, alkyl containing one or more heteroatoms selected from the group consisting of nitrogen, oxygen, sulfur, silicon, and phosphorus, or substituted aryl, and P is hydrogen, and wherein said crosslinked is from about 30 to about 75 percent.

* * * * *